US010287544B2

(12) United States Patent
Bogosian

(10) Patent No.: US 10,287,544 B2
(45) Date of Patent: *May 14, 2019

(54) BACTERIAL FERMENTATION METHODS AND COMPOSITIONS

(71) Applicant: NewLeaf Symbiotics, Inc., St. Louis, MO (US)

(72) Inventor: Gregg Bogosian, Clarkson Valley, MO (US)

(73) Assignee: NEWLEAF SYMBIOTICS, INC., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/894,568

(22) PCT Filed: May 30, 2014

(86) PCT No.: PCT/US2014/040218
§ 371 (c)(1),
(2) Date: Nov. 30, 2015

(87) PCT Pub. No.: WO2014/194189
PCT Pub. Date: Dec. 4, 2014

(65) Prior Publication Data
US 2016/0120188 A1    May 5, 2016

Related U.S. Application Data

(60) Provisional application No. 61/829,987, filed on May 31, 2013.

(51) Int. Cl.
C12N 1/20 (2006.01)
A01N 63/00 (2006.01)

(52) U.S. Cl.
CPC .............. *C12N 1/20* (2013.01); *A01N 63/00* (2013.01)

(58) Field of Classification Search
CPC .................................... C12N 1/20; C12N 1/34
See application file for complete search history.

(56) References Cited

U.S. PATENT DOCUMENTS

| | | |
|---|---|---|
| 4,401,762 A | 8/1983 | Tellier et al. |
| 5,013,665 A | 5/1991 | Suzuki et al. |
| 5,106,648 A | 4/1992 | Williams |
| 5,302,525 A | 4/1994 | Groleau et al. |
| 5,434,062 A | 7/1995 | Groleau et al. |
| 5,512,069 A | 4/1996 | Holland et al. |
| 5,961,687 A | 10/1999 | Joshi et al. |
| 6,107,067 A | 8/2000 | Miller et al. |
| 6,174,837 B1 | 1/2001 | Joshi et al. |
| 6,214,329 B1 * | 4/2001 | Brieva ............... A61K 8/06 424/401 |
| 6,329,320 B1 | 12/2001 | Joshi et al. |
| 6,454,845 B1 * | 9/2002 | Shawcross ............ C09B 47/26 106/31.49 |
| 6,605,430 B1 * | 8/2003 | Affholter ............. C12N 9/0004 435/183 |
| 6,649,721 B1 * | 11/2003 | Dyllick-Brenzinger ............ B01D 19/0404 526/274 |
| 7,435,878 B2 | 10/2008 | Holland |
| 8,153,188 B2 | 4/2012 | Fukuzawa et al. |
| 8,181,388 B2 | 5/2012 | Berger |
| 9,181,541 B2 | 11/2015 | Bogosian |
| 9,845,462 B2 | 12/2017 | Bogosian |
| 2003/0215546 A1 * | 11/2003 | Aguilar ............... A23D 7/0053 426/61 |
| 2005/0054030 A1 * | 3/2005 | Schnoor .................. A62D 3/02 435/41 |
| 2005/0181059 A1 | 8/2005 | Jacob et al. |
| 2006/0228797 A1 | 10/2006 | Holland et al. |
| 2006/0234336 A1 | 10/2006 | Miguez et al. |
| 2007/0031456 A1 * | 2/2007 | Carboulec .......... A61K 39/0225 424/234.1 |
| 2007/0074451 A1 | 4/2007 | Pearce et al. |
| 2010/0034879 A1 * | 2/2010 | Becker ................. A61K 9/0014 424/484 |
| 2011/0269219 A1 | 11/2011 | Holland et al. |
| 2015/0337256 A1 | 11/2015 | Bogosian |
| 2016/0046925 A1 | 2/2016 | Bogosian |
| 2016/0073641 A1 | 3/2016 | Allen et al. |
| 2018/0142230 A1 | 5/2018 | Bogosian |

FOREIGN PATENT DOCUMENTS

| | | | |
|---|---|---|---|
| CN | 101505584 A | 8/2009 | |
| JP | S57-86289 A | 5/1982 | |
| JP | 2009-540825 A | 11/2009 | |
| KR | 20070111915 A * | 11/2007 | |
| WO | WO-9833932 A1 * | 8/1998 | ............. A61K 48/00 |
| WO | 00/060052 A1 | 10/2000 | |

OTHER PUBLICATIONS

Bourque, D. Appl. Microbiol. Biotechnol. 1995. 44: 367-376.*
KR 20070111915. English Abstract. (Year: 2007).*
Abanda-Nkpwatt et al., "Molecular Interaction Between Methylobacterium Extorquens and Seedlings: Growth Promotion, Methanol Consumption, and Localization of the Methanol Emission Site", Journal of Experimental Botany, Oct. 16, 2006, vol. 57 No. 15, pp. 4025-4032.
Chitra et al., "Multigeneric Microbial Coaggregates—Effect of Different Bioformulations of PGPR Cells on the Enhancement of PGPR Characteristics and Biocontrol against Xanthomonas Oryzae pv. Oryzae in Rice Grown Under Lowland Condition", Journal of Applicable Chemistry, 2013, vol. 2 No. 5, pp. 1132-1140.
Corpe et al., "Ecology of the Methylotrophic Bacteria on Living Leaf Surfaces", FEMS Microbiology Ecology, 1989, vol. 62, pp. 243-250.
Corpe et al., "Methanol-Utilizing Bacteria Associated with Green Plants", 1982, Chapter 44, pp. 483-493.

(Continued)

*Primary Examiner* — Renee Claytor
*Assistant Examiner* — Susan E. Fernandez
(74) *Attorney, Agent, or Firm* — Thompson Coburn LLLP; Charles P. Romano

(57) ABSTRACT

The present invention provides methods for the cultivation of the *Methylobacterium* genus of bacteria. In particular the method provides methods for the efficient and inexpensive cultivation of these bacteria. Additionally, the invention provides methods for the utilization of these bacterial cultures to improve plant agriculture.

18 Claims, No Drawings

(56) References Cited

OTHER PUBLICATIONS

Delaney et al. "Development of an Optimized Medium, Strain and High-Throughput Culturing Methods for Methylobacterium Extorquens", PLOS ONE, Apr. 30, 2013, vol. 8, No. 4, e62957.
Green, "Methylobacterium", Prokaryotes, 2006, vol. 5, Chapter 3.1.13, pp. 257-265.
Holland, "Methylobacterium and Plants", Recent Research Developments in Plant Physiology, 1997, pp. 207-213, vol. 1.
International Search Report and Written Opinion for PCT/US2014/040218 dated Oct. 16, 2014.
Jayashree et al., "Evaluation of Pink-Pigmented Facultative Methylotrophic Bacteria for Phosphate Solubilization", Archives of Microbiology, 2011, vol. 193, No. 8, pp. 543-552.
Madhaiyan et al., "Pink-Pigmented Facultative Methylotrophic Bacteria Accelerate Germination, Growth and Yield of Sugarcane Clone Co86032 (*Saccharum officinarum* L.)", Biology and Fertility of Soils, 2005, pp. 350-358, vol. 41.
Maliti et al., "Effects of Methylobacterium Spp. Strains on Rice *Oryza sativa* L Callus Induction, Plantlet Regeneration, and Seedlings Growth in Vitro", Journal of the Torrey Botanical Society, Apr. 2005, vol. 132, No. 2, pp. 355-367.
Vaidehi et al., "Adhesion of Methylobacterium Cells to Rice Roots: Active Metabolism of Micropartner Determines the Degree of Adsorption Level at Rhizosphere", International Journal of Research in Pure and Applied Microbiology, 2012, vol. 2 No. 4, pp. 54-58.
Adegbola, Olufemi "High Cell Density Methanol Cultivation of Methylosinus Trichosporium OB3b", Thesis, Aug. 2008, 95 pgs.
Belanger et al., "Production of Heterologous Protein by Methylobacterium Extorquens in High Cell Density Fermentation", FEMS Microbiology Letters 231, 2004, pp. 197-204.
Dobroth et al., "Polyhydroxybutyrate Synthesis on Biodiesel Wastewater Using Mixed Microbial Consortia", Bioresource Technology, 2011, pp. 3352-3359, vol. 102.
Kane et al., "Unique Susceptibility of Helicobacter pylori to Simethicone Emulsifers in Alimentary Therapeutic Agents", Antimicrobial Agents and Chemotherapy, Feb. 1996, pp. 500-502, vol. 40, No. 2.
Routledge, Sarah "Beyond De-Foaming: The Effects of Antifoams on Bioprocess Productivity", Computational And Structural Biotechnology Journal, Oct. 2012, 7 pgs., vol. 3, Issue 4.
Sigma Product Information, Antifoam SE-15, downloaded from www.sigmaaldrich.com Mar. 4, 2018.
Sigma Product Information, Antifoams, downloaded from www.sigmaaldrich.com Mar. 4, 2018.
Verginer et al., "High Shelf-Life Formulations for Methylobacterium Extorquens DSM 21961, a Microbial Inoculant to Enhance Strawberry Flavour", Multitrophic Interactions in Soil IOBC/wprs Bulletin, 2011, pp. 149-153, vol. 71.
Kim et al., "Improvement in Cell Yield of Methylobacterium sp. by Reducing the Inhibition of Medium Components of Poly-b-Hydroxybutyrate Production", World Journal of Microbiology & Biotechnology, 2003, pp. 357-361, vol. 19.

\* cited by examiner

BACTERIAL FERMENTATION METHODS AND COMPOSITIONS

CROSS-REFERENCE TO RELATED APPLICATION

This application is a 35 U.S.C. § 371 US national stage application of International Patent Application PCT/US2014/040218, filed May 30, 2014, which claims the benefit of U.S. patent application Ser. No. 61/829,987, filed May 31, 2013, the entire disclosures of which are incorporated herein by reference in its entirety.

BACKGROUND

One-carbon organic compounds such as methane and methanol are found extensively in nature, and are utilized as carbon sources by bacteria classified as methanotrophs and methylotrophs. Methanotrophic bacteria include species in the genera *Methylobacter*, *Methylomonas*, *Methylomicrobium*, *Methylococcus*, *Methylosinus*, *Methylocystis*, *Methylosphaera*, *Methylocaldum*, and *Methylocella* (Lidstrom, 2006). Methanotrophs possess the enzyme methane monooxygenase, that incorporates an atom of oxygen from $O_2$ into methane, forming methanol. All methanotrophs are obligate one-carbon utilizers, unable to use compounds containing carbon-carbon bonds. Methylotrophs, on the other hand, can also utilize more complex organic compounds, such as organic acids, higher alcohols, sugars, and the like. Thus, methylotrophic bacteria are facultative methylotrophs. Methylotrophic bacteria include species in the genera *Methylobacterium*, *Hyphomicrobium*, *Methylophilus*, *Methylobacillus*, *Methylophaga*, *Aminobacter*, *Methylorhabdus*, *Methylopila*, *Methylosulfonomonas*, *Marinosulfonomonas*, *Paracoccus*, *Xanthobacter*, *Ancylobacter* (also known as *Microcyclus*), *Thiobacillus*, *Rhodopseudomonas*, *Rhodobacter*, *Acetobacter*, *Bacillus*, *Mycobacterium*, *Arthobacter*, and *Nocardia* (Lidstrom, 2006).

Most methylotrophic bacteria of the genus *Methylobacterium* are pink-pigmented. They are conventionally referred to as PPFM bacteria, being pink-pigmented facultative methylotrophs. Green (2005, 2006) identified twelve validated species in the genus *Methylobacterium*, specifically *M. aminovorans*, *M. chloromethanicum*, *M. dichloromethanicum*, *M. extorquens*, *M. fujisawaense*, *M. mesophilicum*, *M. organophilum*, *M. radiotolerans*, *M. rhodesianum*, *M. rhodinum*, *M. thiocyanatum*, and *M. zatmanii*. However, *M. nidulans* is a nitrogen-fixing *Methylobacterium* that is not a PPFM (Sy et al., 2001). *Methylobacterium* are ubiquitous in nature, being found in soil, dust, fresh water, sediments, and leaf surfaces, as well as in industrial and clinical environments (Green, 2006).

The existence of PPFM bacteria as colonizers of the leaf surfaces of most (if not all) species of plants (ranging from algae, mosses and liverworts, and angiosperms and gymnosperms) suggests that PPFM bacteria may play an important role in plant physiology (Corpe and Rheem, 1989; Holland and Polacco, 1994; Holland, 1997; Kutschera, 2007). The fact that plants produce and excrete methanol, probably as a waste product of pectin metabolism in growing plant cell walls, suggested to these researchers that a symbiotic relationship exists, with the PPFM bacteria feeding on the plant-produced methanol and in turn providing positive benefits to the plants. The suggested benefits of PPFM bacteria on plant physiology include positive effects on nitrogen metabolism, seed germination, and stimulation of plant growth through the provision of PPFM-generated cytokinin plant hormones. The use of PPFM bacteria to improve plant growth, plant yield, seed germination, male fertility, and plant nutritional qualities has been disclosed in U.S. Pat. No. 5,512,069, U.S. Pat. No. 5,961,687, U.S. Pat. No. 6,174,837, U.S. Pat. No. 6,329,320, U.S. Pat. No. 7,435,878, and US Patent Application Pub. No. 2006/0228797. In addition, PPFM bacteria have been found to increase the yield of cultivated algae, suggesting their application to the production of algae-derived biofuels (US Patent Application Pub. No. 2011/0269219).

The broad application of *Methylobacterium* to row crops, vegetables, and other cultivated plants, as well as in the production of algae-based biofuels, would require the efficient and inexpensive cultivation of enormous quantities of *Methylobacterium* cultures. Other industrial applications of *Methylobacterium* may also benefit from efficient *Methylobacterium* production techniques. Such industrial applications include the use of *Methylobacterium* as environmental pollution indicators (as certain *Methylobacterium* can grow on soot) and as irradiation-quality-control monitors in the packaged food industries (as certain *Methylobacterium* exhibit high resistance to gamma-ray irradiation). Other industrial applications include the use of *Methylobacterium* to degrade environmental pollutants (U.S. Pat. No. 5,418, 161, U.S. Pat. No. 5,487,834, U.S. Pat. No. 6,107,067, U.S. Pat. No. 7,214,509), to produce useful industrial compounds, polymeric precursors, or biopolymers (U.S. Pat. No. 5,236,930, U.S. Pat. No. 5,686,276, U.S. Pat. No. 6,107, 067), and recombinant proteins (US Patent Application Pub. No. 20060234336).

However, various publications in the subject area of PPFM cultivation suggest that there are significant obstacles to overcome in order to achieve the efficient and inexpensive large-scale cultivation of these bacteria. Holland and Polacco (1994) reported that "isolated PPFMs do not grow well on plant tissue culture media", a medium which is rich in nutrients, and that "PPFMs are slow growers". Madhaiyan et al. (2004) state of PPFM bacteria that "Their slow-growing nature and distribution over the whole plant suggest that their numbers are regulated simply by dilution as the plant tissue expands away from growing points." Abanda-Nkpwatt et al. (2006) reported of growth of PPFM bacteria that "in liquid culture, the solution became turbid within 4-5 days" without specifying the titer achieved (titer referring to the number of bacterial cells, or colony-forming units, per milliliter).

These consistent reports of slow growth are further confirmed and expanded upon by other studies indicating that PPFM bacteria could only be grown to relatively low titers. These growth studies were in standard liquid microbiological media, which are purposely prepared so as to be "water-clear". Such media permit the visual observation and detection of both desired and undesired (i.e. contaminating) microbial growth, manifest as the development of turbidity visible to the naked eye.

Corpe and Basile (1982) presented a systematic investigation of the growth responses of various PPFM bacteria to a wide variety of carbon sources. They utilized as their base medium the standard mineral base employed by Stanier et al. (1966). In that publication, Stanier et al. stated of their base medium that "It is heavily chelated with nitriloacetic acid and EDTA, and forms a copious precipitate upon autoclaving. The precipitate redissolves as the medium cools, to form a water-clear solution."

Using this "water-clear" solution as their base medium, Corpe and Basile (1982) tested a wide variety of carbon sources for their ability to support the growth of PPFM bacteria. They found several carbon sources that were relatively better than all the others, namely glycerol, glutamate, methanol, glucose, aspartate, succinate and malate. However, even after 7 days of incubation (the time allotted to each growth test), none of the cultures achieved an optical density (at 660 nanometers, the standard wavelength to measure microbial growth) of greater than 0.7 optical units, and most were well below this density. Sy et al. (2005) reported that a suspension of PPFM bacteria with an optical density of about 0.05 optical units contained about $5 \times 10^6$ colony forming units (CFU) of PPFM bacteria per milliliter. Thus, the maximum titer that Corpe and Basile achieved after one week of incubation with the best carbon sources they identified was about $7 \times 10^7$ colony-forming units per milliliter.

Sy et al. (2005) also reported that with a minimal salts medium containing succinate as the carbon source, they achieved a final titer of $M.$ $extorquens$ of about $2.5 \times 10^8$ colony-forming-units per milliliter.

Corpe and Rheem (1989) reported that PPFM bacteria "had a much longer doubling time than other leaf heterotrophs, in nutrient broth and other common heterotrophic media", and concluded that methanol produced by plants "may allow the PPFMs to compete successfully" with other bacteria on leaf surfaces. The maximum titer that Corpe and Reehm achieved (after an unspecified incubation period) was about $3 \times 10^8$ colony-forming units per milliliter.

Thus, these publications indicate that in standard "water-clear" microbiological growth media, the growth of PPFM bacteria is slow and typically plateaus at a relatively low final titer of about $3 \times 10^8$ colony-forming units per milliliter.

In order to meet the potential needs for PPFM bacteria for commercial applications in row crops, vegetables, and other cultivated plants, as well as in the production of algae-based biofuels, manufacturing capabilities would need to produce enormous quantities of these bacteria.

Taking corn as just one example, there are about 40 million hectares of corn grown each year in the United States. For each 1% of market penetration (400,000 hectares) in this single nation and on this single crop, the need for PPFM bacteria can be estimated to be in the range of about 30 liters per hectare of PPFM culture with a titer of about $3 \times 10^8$ colony-forming units per milliliter, applied either as a seed treatment or as a foliar spray. This equates to about 12 million liters of PPFM culture at that titer being required each year to treat 1% of the United States corn crop. If the production time per batch was 7 days, a facility with even the largest volume fermenters on the market (producing 60,000 liters per batch) running at full capacity (about 250 days per year) would require 5 or 6 of these huge fermenters (again, just to supply the need for 1% market penetration of corn in the United States). Such a facility probably could not be built and operated in a commercially viable manner.

Thus, there exists a need for the development of efficient and inexpensive large-scale production of *Methylobacterium*.

SUMMARY

Provided herein are methods for efficient production of large quantities of *Methylobacterium*. These methods can result in high titer *Methylobacterium* cultures where production time per batch is significantly reduced. The methods of *Methylobacterium* production provided herein can also use culture medium comprised of inexpensive and readily available components. Also provide herein are useful fermentation broths, fermentation broth products, fermentation products, and compositions comprising *Methylobacterium*. Methods of using the fermentation broths, fermentation broth products, fermentation products, and compositions comprising *Methylobacterium* to treat plants or plant parts are also provided herein. The methods and compositions provided herein can be used to produce large quantities of *Methylobacterium* for application to plants or plant parts, for use as an inoculum in bioremediation, for production of useful products, and for production of recombinant proteins. Useful products obtainable by the methods and compositions provided herein include, but are not limited to, poly-3-hydroxy butyric acid, 1,3-propanediol, and oxazopyrroloquinolines.

Methods for obtaining a *Methylobacterium* preparation comprising growing *Methylobacterium* in an emulsion comprising a continuous phase and a dispersed phase that is immiscible or only partially miscible in the continuous phase are provided herein. In certain embodiments, the *Methylobacterium* is a mono-culture or co-culture of *Methylobacterium*. In certain embodiments, the (a) the dispersed phase comprises a non-aqueous liquid and the continuous phase comprises an aqueous liquid or (b) the dispersed phase comprises an aqueous liquid and the continuous phase comprise a non-aqueous liquid. In certain embodiments, the non-aqueous liquid has a miscibility in water that is equal to or less than that of n-pentanol at 25° C. In certain embodiments, the dispersed phase provides for an increased yield of said *Methylobacterium* relative to a yield obtained by growing the *Methylobacterium* under identical conditions except for being grown in a non-emulsion that comprises a liquid corresponding to that of the continuous phase. In certain embodiments, the methods further comprise harvesting *Methylobacterium* grown in the media. In certain embodiments, the emulsion further comprises an emulsifier in an amount sufficient to stabilize the emulsion. In certain embodiments, the emulsifier is selected from the group consisting of thickeners, surfactants, and combinations thereof. In certain embodiments of any of the aforementioned methods, the non-aqueous liquid comprises an alcohol, an aldehyde, a ketone, a fatty acid, a phospholipid, or any combination thereof. In certain embodiments, the alcohol is selected from the group consisting of aliphatic alcohols containing at least 5 carbons and sterols. In certain embodiments of any of the aforementioned methods, the non-aqueous liquid comprises one or more animal, microbial, synthetic, or plant oils. In certain embodiments, the plant oil is selected from the group consisting of corn, soybean, cotton, peanut, sunflower, olive, flax, coconut, palm, rapeseed, sesame seed, safflower, and combinations thereof. In certain embodiments of any of the aforementioned methods, the emulsion does not contain a photosynthetic microorganism. In certain embodiments of any of the aforementioned methods, the emulsion further comprises one or more non-photosynthetic microorganisms of predetermined identity other than *Methylobacterium*. In certain embodiments of any of the aforementioned methods, the dispersed phase comprises at least about 0.02% to about 20% of said emulsion by mass. In certain embodiments of any of the aforementioned methods, the non-aqueous liquid is an agriculturally acceptable adjuvant or agriculturally acceptable excipient. In certain embodiments of any of the aforementioned methods, the growing comprises the steps of inoculating said emulsion with said *Methylobacterium* and incubating said inoculated emulsion under conditions sufficient to provide for growth of said *Methylobacterium*. In certain embodiments of any of the aforementioned methods, the *Methylobacterium* is selected from the group consisting of *M. aminovorans, M. chloromethanicum, M. dichloromethanicum, M. extorquens, M. fujisawaense, M. mesophilicum, M. organophilum, M. radiotolerans, M. rhodesianum, M. rhodinum, M. thiocyanatum, M. nodulans, M. cerastii, M. gossipiicola, Methylobacterium* sp. strain LMG6378, *M. phyllosphaerae, M. oryzae, M. platani, M. populi,* and *M. zatmanii*. In certain embodiments of any of the aforementioned methods, the emulsion is essentially free of contaminating microorganisms. In certain embodiments of any of the aforementioned methods, the method further comprises recovering all or a portion of the *Methylobacterium* from the emulsion. In certain embodiments of any of the aforementioned methods, the method further comprises dehydrating the recovered portion of the *Methylobacterium*.

Also provided are *Methylobacterium* preparations obtained by the any of the aforementioned methods, wherein either the dispersed phase or the continuous phase comprises a non-aqueous liquid that has a miscibility in water that is equal to or less than that of n-pentanol at 25° C.

Also provided are methods for treating a plant or a plant part with *Methylobacterium* comprising the step of applying to said plant or plant part a composition comprising any of the aforementioned *Methylobacterium* preparations. In certain embodiments, the composition further comprises an agriculturally acceptable adjuvant or an agriculturally acceptable excipient. In certain embodiments of any of the aforementioned methods, the composition lacks a solid substance. In certain embodiments, the plant part is a seed and said composition has a *Methylobacterium* titer of at least about $5 \times 10^8$ colony-forming units per gram of said composition to about $5 \times 10^{13}$ colony-forming units per gram of said composition. In certain embodiments, the plant part is a seed, stem, root, flower, cotyledon, a coleoptile, fruit, or a leaf. In certain embodiments, the plant or plant part is a corn, *Brassica* sp., alfalfa, rice, rye, sorghum, pearl millet, proso millet, foxtail millet, finger millet, sunflower, safflower, soybean, tobacco, potato, peanuts, cotton, sweet potato, cassava, coffee, coconut, pineapple, citrus trees, cocoa, tea, banana, avocado, fig, guava, mango, olive, papaya, cashew, macadamia, almond, sugar beet, sugarcane, oat, barley, tomato, lettuce, green bean, lima bean, pea, cucurbit, ornamental, or conifer plant or plant part. In certain embodiments, the plant or plant part is at least partially coated with an aforementioned *Methylobacterium* preparation. Also provided herein are processed plant products obtained from any of the aforementioned plants or plant parts, wherein said processed product contains the emulsion. In certain embodiments, the processed plant product is a meal, paste, flour, flake, or feed. In certain embodiments, the processed product is non-regenerable.

Provided herein are fermentation products that comprise an emulsion comprising a continuous phase and a dispersed phase that is immiscible or only partially miscible in the continuous phase, and a mono-culture or co-culture of *Methylobacterium*. In certain embodiments, the (a) the dispersed phase comprises a non-aqueous liquid and the continuous phase comprises an aqueous liquid or (b) the dispersed phase comprises an aqueous liquid and the continuous phase comprise a non-aqueous liquid. In certain embodiments, the non-aqueous liquid has a miscibility in water that is equal to or less than that of n-pentanol at 25° C. In certain embodiments, the fermentation product is essentially free of contaminating microorganisms. In certain embodiments, the fermentation product further comprises one or more microorganisms of pre-determined identity other than *Methylobacterium*. In certain embodiments, the fermentation product lacks a solid substance. In certain embodiments, the fermentation product does not contain a photosynthetic microorganism. In certain embodiments, the *Methylobacterium* are at a titer of at least about $5 \times 10^7$, colony-forming units per milliliter, at least about $5 \times 10^8$ colony-forming units per milliliter, at least about $1 \times 10^9$ colony-forming units per milliliter, at least about $1 \times 10^{10}$ colony-forming units per milliliter, or at least about $3 \times 10^{10}$ colony-forming units per milliliter. In certain embodiments, the *Methylobacterium* are at a titer of at least about $5 \times 10^7$ colony-forming units per milliliter to at least about $6 \times 10^{10}$ colony-forming units per milliliter. In certain embodiments, at least one of the *Methylobacterium* is a Pink Pigmented Facultative Methylotroph (PPFM). In certain embodiments, the Pink Pigmented Facultative Methylotroph (PPFM) is selected from the group consisting of *M. aminovorans, M. chloromethanicum, M. dichloromethanicum, M. extorquens, M. fujisawaense, M. mesophilicum, M. organophilum, M. radiotolerans, M. rhodesianum, M. rhodinum, M. thiocyanatum, M. cerastii, M. gossipiicola, Methylobacterium* sp. strain LMG6378, *M. phyllosphaerae, M. oryzae, M. platani, M. populi,* and *M. zatmanii*. In certain embodiments, at least one of the *Methylobacterium* is *M. nodulans*.

Also provided are compositions that comprise an emulsion comprising a continuous phase and a dispersed phase, and a mono-culture or co-culture of *Methylobacterium*. In certain embodiments, the (a) the dispersed phase comprises a non-aqueous liquid and the continuous phase comprises an aqueous liquid or (b) the dispersed phase comprises an aqueous liquid and the continuous phase comprise a non-aqueous liquid. In certain embodiments, the non-aqueous liquid has miscibility in water that is equal to or less than that of n-pentanol at 25° C. In certain embodiments, the composition is essentially free of contaminating microorganisms. In certain embodiments, the composition further comprises at least one of an agriculturally acceptable adjuvant and/or an agriculturally acceptable excipient. In certain embodiments, the composition lacks a solid substance. In certain embodiments, the second liquid comprises an alcohol, an aldehyde, a ketone, a fatty acid, a phospholipid, or any combination thereof. In certain embodiments, the alcohol is selected from the group consisting of aliphatic alcohols containing at least 5 carbons and sterols. In certain embodiments, the non-aqueous liquid comprises one or more plant oils. In certain embodiments, the plant oil is selected from the group consisting of corn, soybean, cotton, peanut, sunflower, olive, flax, coconut, palm, rapeseed, sesame seed, safflower, and combinations thereof. In certain embodiments, the solid substance further comprises an agriculturally acceptable adjuvant or an agriculturally acceptable excipient. In certain embodiments, the composition does not contain a photosynthetic microorganism. In certain embodiments, the composition further comprises at least one pesticide and/or at least one bacteriostatic agent. In certain embodiments, the pesticide is selected from the group consisting of an insecticide, a fungicide, a nematocide, and a bacteriocide, wherein said pesticide does not substantially inhibit growth of said *Methylobacterium*.

Also provided herein are methods for treating a plant or a plant part with *Methylobacterium* comprising the step of applying to said plant or plant part any of the aforementioned fermentation products or compositions. In certain embodiments of the methods, the plant part is a seed, stem, root, flower, cotyledon, a coleoptile, fruit, or a leaf. In certain embodiments of the methods, plant or plant part is a corn, *Brassica* sp., alfalfa, rice, rye, sorghum, pearl millet, proso millet, foxtail millet, finger millet, sunflower, safflower, soybean, tobacco, potato, peanuts, cotton, sweet potato, cassava, coffee, coconut, pineapple, citrus trees, cocoa, tea, banana, avocado, fig, guava, mango, olive, papaya, cashew, macadamia, almond, sugar beet, sugarcane, oat, barley, tomato, lettuce, green bean, lima bean, pea, cucurbit, ornamental, or conifer plant or plant part. In certain embodiments of the methods, the plant part is a seed and the composition has a *Methylobacterium* titer of at least about $5 \times 10^7$ colony-forming units per gram of the composition to about $6 \times 10^{10}$, $3 \times 10^{12}$, $5 \times 10^{12}$, $1 \times 10^{13}$, or $5 \times 10^{13}$ colony-forming units per gram of the composition.

Plants or plant parts obtained by the methods, wherein the plant or plant part is at least partially coated with the fermentation product of the composition, are also provided.

A plant or plant part, wherein the plant or plant part is at least partially coated with an emulsion comprising a first aqueous liquid, a second liquid having a miscibility in water that equal to or less than that of n-pentanol, and a mono-culture or co-culture of an exogenous *Methylobacterium*. Processed plant products obtained from the plants or plant parts obtained by any of the aforementioned plant or plant parts, wherein the processed product contains any of the aforementioned emulsions, fermentation products, fermentation broths, or compositions are also provided herein. In certain embodiments, the processed plant product is a meal, paste, flour, flake, or feed. In certain embodiments, the processed plant product is non-regenerable.

Also provided are methods for producing an industrial product comprising growing a mono-culture or co-culture of *Methylobacterium* in an emulsion comprising a continuous phase and a dispersed phase that is immiscible or only partially miscible in the continuous phase and harvesting the industrial product after growing the *Methylobacterium*. In certain embodiments, the emulsion comprises a first aqueous liquid and a second non-aqueous liquid that is immiscible or only partially miscible in the first aqueous liquid. In certain embodiments, the emulsion is essentially free of contaminating microorganisms, from the solid phase, the liquid phase, or the combination thereof. In certain embodiments, the industrial product is a polymeric precursor, a biopolymer, a precursor of a medicinal compound, a medicinal compound, or a recombinant protein. In certain embodiments of any of the aforementioned methods, the industrial product is poly-3-hydroxy butyric acid, 1,3-propanediol, a pyrroloquinolinequinone, or an oxazopyrroloquinoline. In certain embodiments of any of the aforementioned methods, the emulsion does not contain a photosynthetic microorganism.

DESCRIPTION

Definitions

As used herein, the phrases "adhered thereto" and "adherent" refer to *Methylobacterium* that are associated with a solid substance by growing, or having been grown, on a solid substance.

As used herein, the phrase "agriculturally acceptable adjuvant" refers to a substance that enhances the performance of an active agent in a composition for treatment of plants and/or plant parts. In certain compositions, an active agent can comprise a mono-culture or co-culture of *Methylobacterium*.

As used herein, the phrase "agriculturally acceptable excipient" refers to an essentially inert substance that can be used as a diluent and/or carrier for an active agent in a composition for treatment of plants. In certain compositions, an active agent can comprise a mono-culture or co-culture of *Methylobacterium*.

As used herein, the term "algae" refers to any type of micro- or macroalgae.

As used herein, the term "*Methylobacterium*" refers to bacteria that are facultative methylotrophs of the genus *Methylobacterium*. The term *Methylobacterium*, as used herein, thus does not encompass include species in the genera *Methylobacter, Methylomonas, Methylomicrobium, Methylococcus, Methylosinus, Methylocystis, Methylosphaera, Methylocaldum*, and *Methylocella*, which are obligate methanotrophs.

As used herein, the phrase "co-culture of *Methylobacterium*" refers to a *Methylobacterium* culture comprising at least two strains of *Methylobacterium* or at least two species of *Methylobacterium*.

As used herein, the phrase "contaminating microorganism" refers to microorganisms in a culture, fermentation broth, fermentation broth product, or composition that were not identified prior to introduction into the culture, fermentation broth, fermentation broth product, or composition.

As used herein, the term "emulsion" refers to a colloidal mixture of two immiscible liquids wherein one liquid is the continuous phase and the other liquid is the dispersed phase. In certain embodiments, the continuous phase is an aqueous liquid and the dispersed phase is a non-aqueous liquid that is not miscible in the aqueous liquid.

As used herein, the phrase "essentially free of contaminating microorganisms" refers to a culture, fermentation broth, fermentation product, or composition where at least about 95% of the microorganisms present by amount or type in the culture, fermentation broth, fermentation product, or composition are the desired *Methylobacterium* or other desired microorganisms of pre-determined identity.

As used herein, the phrase "inanimate solid substance" refers to a substance which is insoluble or partially soluble in water or aqueous solutions and which is either non-living or which is not a part of a still-living organism from which it was derived.

As used herein, the phrase "mono-culture of *Methylobacterium*" refers to a *Methylobacterium* culture consisting of a single strain of *Methylobacterium*.

As used herein, a "pesticide" refers to an agent that is insecticidal, fungicidal, nematocidal, bacteriocidal, or any combination thereof.

As used herein, the phrase "bacteriostatic agent" refers to agents that inhibit growth of bacteria but do not kill the bacteria.

As used herein, the phrase "pesticide does not substantially inhibit growth of said *Methylobacterium*" refers to any pesticide that when provided in a composition comprising a fermentation product wherein a mono-culture or co-culture of *Methylobacterium*, results in no more than a 50% inhibition of *Methylobacterium* growth when the composition is applied to a plant or plant part in comparison to a composition lacking the pesticide. In certain embodiments, the pesticide results in no more than a 40%, 20%, 10%, 5%, or 1% inhibition of *Methylobacterium* growth when the composition is applied to a plant or plant part in comparison to a composition lacking the pesticide.

As used herein, the term "PPFM bacteria" refers without limitation to bacterial species in the genus *Methylobacterium* other than *M. nodulans*.

As used herein, the phrase "solid substance" refers to a substance which is insoluble or partially soluble in water or aqueous solutions.

As used herein, the phrase "solid phase that can be suspended therein" refers to a solid substance that can be distributed throughout a liquid by agitation.

As used herein, the term "non-regenerable" refers to either a plant part or processed plant product that cannot be regenerated into a whole plant.

As used herein, the phrase "substantially all of the solid phase is suspended in the liquid phase" refers to media wherein at least 95%, 98%, or 99% of solid substance(s) comprising the solid phase are distributed throughout the liquid by agitation.

As used herein, the phrase "substantially all of the solid phase is not suspended in the liquid phase" refers to media where less than 5%, 2%, or 1% of the solid is in a particulate form that is distributed throughout the media by agitation.

As used herein, the term "yield", when used in reference to *Methylobacterium* obtained in a fermentation, refers to the numbers of *Methylobacterium* obtained. Methods for determining such yield include, but are not limited to, determining the numbers of colony forming units (CFU) per unit volume or unit mass of material obtained, determining a wet weight of the *Methylobacterium* obtained, and/or determining a dry weight of the *Methylobacterium* obtained.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Methods for Culturing *Methylobacterium*, Compositions, and Uses Thereof

Methods where *Methylobacterium* are cultured in media comprising an emulsion have been found to significantly increase the resultant yield of *Methylobacterium* relative to methods where the *Methylobacterium* are cultured in liquid media alone. In certain embodiments, the methods can comprise growing the *Methylobacterium* in an emulsion under conditions that provide for *Methylobacterium* growth. Medias comprising the emulsion and *Methylobacterium* can be obtained by a variety of methods that include, but are not limited to, any of: (a) inoculating a c media comprising the emulsion with *Methylobacterium*; (b) inoculating the aqueous liquid with *Methylobacterium*, introducing the non-aqueous liquid, and mixing to form an emulsion; or (c) the combination of (a) and (b). In certain embodiments, the growing comprises the steps of inoculating the media with the *Methylobacterium* and incubating the inoculated media under conditions sufficient to provide for growth of the *Methylobacterium*. In certain embodiments, the *Methylobacterium* are inoculated into the media at a titer of at least about $5 \times 10^4$ colony-forming units per milliliter or at least about $1 \times 10^5$ colony-forming units per milliliter. In certain embodiments, the *Methylobacterium* is selected from the group consisting of *M. aminovorans*, *M. chloromethanicum*, *M. dichloromethanicum*, *M. extorquens*, *M. fujisawaense*, *M. mesophilicum*, *M. organophilum*, *M. radiotolerans*, *M. rhodesianum*, *M. rhodinum*, *M. thiocyanatum*, *M. nodulans*, *M. cerastii*, *M. gossipiicola*, *Methylobacterium* sp. strain LMG6378, *M. phyllosphaerae*, *M. oryzae*, *M. platani*, *M. populi*, and *M. zatmanii*. The methods can also further comprise the steps of harvesting the mono- or co-culture of *Methylobacterium*. Methods for harvesting the *Methylobacterium* can include, but are not limited to, separating the *Methylobacterium* from the liquid phase by filtration, centrifugation, decanting, and the like.

Agitation methods that can be used include, but are not limited to, stirring, reciprocal shaking, rotary shaking, and combinations thereof. In certain embodiments, agitation can comprise placing media comprising the emulsion on a rotary shaker that provides at least 25, 50, 100, 200, 250, 500, or 1000 revolutions per minute (RPM). Agitation equivalent to that provided by a rotary shaker set at least at 25, 50, 100, 200, 250, 500, or 1000 revolutions per minute (RPM) can also be obtained by stirring, reciprocal shaking, and other methods. In certain embodiments, separation of the aqueous and non-aqueous liquids in the emulsion can be eliminated or reduced upon agitation equivalent to that provided by a rotary shaker set at least at 25, 50, 100, 200, 250, 500, or 1000 revolutions per minute (RPM).

Fermentation broths comprising emulsions that are used in the methods provided herein can be axenic cultures that are essentially free of contaminating microorganisms. In certain embodiments, at least about 95%, 98%, 99%, 99.5%, 99.8%, 99.9%, or 100% of the microorganisms present by amount or type in the culture, fermentation broth, fermentation product, or compositions provided herein are the desired *Methylobacterium* or other desired microorganisms of pre-determined identity. Desired *Methylobacterium* or other desired microorganisms of pre-determined identity are microorganisms obtained from a pure culture. To provide for such axenic cultures, the components used in the culture media comprising the emulsion are sterilized or obtained in an essentially sterile form prior to inoculation of *Methylobacterium* and/or any additional desired microorganisms in the mono- or co-culture. Sterilization of various components of the media comprising the emulsion can be achieved by methods including, but not limited to, autoclaving, irradiation, filter sterilization (for liquids), and the like. A culture, fermentation broth, fermentation product, or composition that is essentially free of contaminating microorganisms can be obtained where the liquid or liquid and any added solid components of that culture, fermentation broth, fermentation product, or composition were sterile prior to the inoculation or provision of the desired microorganisms of pre-determined identity and suitable steps are taken to avoid contamination of the culture during growth of the desired microorganisms or contamination of the composition.

Methods provided herein where *Methylobacterium* are cultured in media comprising an emulsion can be practiced in any of a batch-mode fermentation, a fed-batch mode fermentation, or a continuous fermentation. Fermentation broths, fermentation broth products, and compositions provided herein can also be obtained from any of a batch-mode fermentation, a fed-batch mode fermentation, or a continuous fermentation. In certain embodiments, factors such as the pH and oxygen concentration can be controlled in any of the batch-mode fermentation, fed-batch mode fermentation, or continuous fermentation processes used in the methods provided herein.

Monocultures or co-cultures of *Methylobacterium* and resultant fermentation broths, fermentation broth products, and compositions provided herein can comprise one or more *Methylobacterium* that include, but are not limited to, *M. aminovorans*, *M. chloromethanicum*, *M. dichloromethanicum*, *M. extorquens*, *M. fujisawaense*, *M. mesophilicum*, *M. organophilum*, *M. radiotolerans*, *M. rhodesianum*, *M. rhodinum*, *M. thiocyanatum*, *M. nodulans*, *M. cerastii*, *M. gossipiicola*, *Methylobacterium* sp. strain LMG6378, *M. phyllosphaerae*, *M. oryzae*, *M. platani*, *M. populi*, and *M. zatmanii*. In certain embodiments, monocultures or co-cultures of *Methylobacterium* and resultant fermentation broths and fermentation broth products provided herein can consist of one or more *Methylobacterium*. However, the methods provided herein can also be used on other *Methylobacterium*. *Methylobacterium* can also be obtained by various published methods (Madhaiyan et al., 2007). In certain embodiments, such other *Methylobacterium* that can be used will be *Methylobacterium* having 16S RNA sequences of at least about 60%, 70%, 80%, 90%, or 95% sequence identity to the 16S RNA sequences of other known *Methylobacterium*. Typing of *Methylobacterium* by use of 16S RNA sequence comparisons is at least described by Cao et al, 2011. In certain embodiments, the mono-cultures or co-cultures and resultant products can comprise a *Methylobacterium* that can colonize plants and/or plant parts. *Methylobacterium* that can colonize plants and/or plant parts include, but are not limited to, *M. extorquens, M. nodulans*, and *M. mesophilicum. Methylobacterium* that can colonize plants and/or plant parts also include, but are not limited to, *Methylobacterium cerastii* species (with a representative strain available as DSM 23679 from the Leibniz Institute DSMZ-German Collection of Microorganisms and Cell Cultures ("DSMZ"), Braunschweig, Germany), *Methylobacterium gossipiicola* species (with a representative strain available as NRRL B-51692 from the USDA ARS, Peoria, Ill., USA), *Methylobacterium* sp. strain LMG6378 (available from the Belgian Co-ordinated Collection of Micro-organisms/Laboratorium voor Microbiologie ("BCCLM") Ghent, Belgium), *Methylobacterium phyllosphaerae* species (with a representative strain available as available as DSM 19779T from the DSMZ), *Methylobacterium oryzae* species (with a representative strain available as DSM 18207T from the DSMZ), *Methylobacterium nodulans* species (with a representative strain available as LMG 21967 from the BCCLM), *Methylobacterium platani* species (with a representative strain available as KCTC 12901 from the Korean Collection for Type Cultures, Yusong-Ku, Taejon, K R ("KCTC"), and *Methylobacterium populi* species (with a representative strain available as ATCC BAA-705 from the ATCC). Fermentation broths, fermentation broth products, compositions, methods of making the same, and methods of using the same, including, but not limited to, methods of treating plants, where the *Methylobacterium* is a *Methylobacterium* that can colonize a plant and/or a plant part that is selected from the group consisting of *M. extorquens, M. nodulans, M. mesophilicum, M. cerastii, M. gossipiicola, Methylobacterium* sp. strain LMG6378, *M. phyllosphaerae, M. oryzae, M. platani*, and *M. populi* are thus provided. Methods of isolating other *Methylobacterium* that can colonize plants and/ or plant parts have been described in various publications and can also be used (see Madhaiyan et al., and references cited therein). Without seeking to be limited by theory, it is believed that the methods of culturing *Methylobacterium* in media comprising an emulsion provided herein can be especially advantageous for growing *Methylobacterium* that can colonize plants and/or plant parts or that were isolated from the surfaces of plants and/or plant parts.

Representative *Methylobacterium* that can be used in the fermentation broths, fermentation broth products, compositions and related methods provided herein include, but are not limited to, the *Methylobacterium* of Table 1.

TABLE 1

Representative *Methylobacterium*

| *Methylobacterium* | Depository Accession Numbers for Type Strain |
|---|---|
| *Methylobacterium adhaesivum* | AR27 = CCM 7305 = CECT 7069 = DSM 17169T = KCTC 22099T |
| *Methylobacterium aerolatum* | DSM 19013 = JCM 16406 = KACC 11766 |
| *Methylobacterium aminovorans* | ATCC 51358 = CIP 105328 = IFO (now NBRC) 15686 = JCM 8240 = VKM B-2145 |
| *Methylobacterium aquaticum* | CCM 7218 = CECT 5998 = CIP 108333 = DSM 16371 |
| *Methylobacterium brachiatum* | DSM 19569 = NBRC 103629 = NCIMB 14379 |
| *Methylobacterium bullatum* | DSM 21893 = LMG 24788 |
| *Methylobacterium cerastii* | CCM 7788 = CCUG 60040 = DSM 23679 |
| *Methylobacterium chloromethanicum* | NCIMB 13688 = VKM B-2223 |
| *Methylobacterium dichloromethanicum* | CIP 106787 = DSM 6343 = VKM B-2191 |
| *Methylobacterium extorquens* | ATCC 43645 = CCUG 2084 = DSM 1337 = IAM 12631 = IFO (now NBRC) 15687 = JCM 2802 = NCCB 78015 = NCIB (now NCIMB) 9399 = VKM B-2064. |
| *Methylobacterium fujisawaense* | ATCC 43884 = CIP 103775 = DSM 5686 = IFO (now NBRC) 15843 = JCM 10890 = NCIB (now NCIMB) 12417 |
| *Methylobacterium gossipiicola* | CCM 7572 = NRRL B-51692 |
| *Methylobacterium gregans* | DSM 19564 = NBRC 103626 = NCIMB 14376 |
| *Methylobacterium hispanicum* | GP34 = CCM 7219 = CECT 5997 = CIP 108332 = DSM 16372 |
| *Methylobacterium iners* | DSM 19015 = JCM 16407 = KACC 11765 |
| *Methylobacterium isbiliense* | CCM 7304 = CECT 7068 |
| *Methylobacterium jeotgali* | KCTC 12671 = LMG 23639 |
| *Methylobacterium komagatae* | DSM 19563 = NBRC 103627 = NCIMB 14377 |
| *Methylobacterium longum* | CECT 7806 = DSM 23933 |
| *Methylobacterium lusitanum* | DSM 14457 = NCIMB 13779 = VKM B-2239 |
| *Methylobacterium marchantiae* | CCUG 56108 = DSM 21328 |
| *Methylobacterium mesophilicum* | ATCC 29983 = CCUG 16482 = CIP 101129 = DSM 1708 = ICPB 4095 = IFO (now NBRC) 15688 = JCM 2829 = LMG 5275 = NCIB (now NCIMB) 11561 = NRRL B-14246 |
| *Methylobacterium nodulans* | LMG 21967 = ORS 2060 |
| *Methylobacterium organophilum* | ATCC 27886 = CIP 101049 = DSM 760 = HAMBI 2263 = IFO (now NBRC) 15689 = JCM 2833 = LMG 6083 = NCCB 78041 = VKM B-2066 |

TABLE 1-continued

Representative *Methylobacterium*

| *Methylobacterium* | Depository Accession Numbers for Type Strain |
|---|---|
| *Methylobacterium oryzae* | DSM 18207 = JCM 16405 = KACC 11585 = LMG 23582 |
| *Methylobacterium persicinum* | DSM 19562 = NBRC 103628 = NCIMB 14378 |
| *Methylobacterium phyllosphaerae* | DSM 19779 = JCM 16408 = KACC 11716 = LMG 24361 |
| *Methylobacterium platani* | JCM 14648 = KCTC 12901 |
| *Methylobacterium podarium* | ATCC BAA-547 = DSM 15083 |
| *Methylobacterium populi* | ATCC BAA-705 = NCIMB 13946 |
| *Methylobacterium radiotolerans* | ATCC 27329 = CIP 101128 = DSM 1819 = IFO (now NBRC) 15690 = JCM 2831 = LMG 2269 = NCIB (now NCIMB) 10815 = VKM B-2144 |
| *Methylobacterium rhodinum* | ATCC 14821 = CIP 101127 = DSM 2163 = IFO (now NBRC) 15691 = JCM 2811 = LMG 2275 = NCIB (now NCIMB) 9421 = VKM B-2065 |
| *Methylobacterium suomiense* | DSM 14458 = NCIMB 13778 = VKM B-2238 |
| *Methylobacterium tardum* | DSM 19566 = NBRC 103632 = NCIMB 14380 |
| *Methylobacterium thiocyanatum* | ATCC 700647 = DSM 11490 = JCM 10893 = VKM B-2197 |
| *Methylobacterium variabile* | CCM 7281 = CECT 7045 = DSM 16961 |
| *Methylobacterium zatmanii* | ATCC 43883 = CCUG 36916 = CIP 103774 = DSM 5688 = IFO (now NBRC) 15845 = JCM 10892 = LMG 6087 = NCIB (now NCIMB) 12243 = VKM B-2161 |

Depository Key
ATCC: American Type Tissue Culture Collection, Manassas, VA, USA
CCUG: Culture Collection, University of Göteborg, Sweden
CIP: Collection de l'Institut Pasteur, Paris, FR
DSM: DSMZ-German Collection of Microorganisms and Cell Cultures ("DSMZ"), Braunschweig, Germany
JCM: Japan Collection of Microorganisms, Saitama, Japan
LMG: Belgian Co-ordinated Collection of Micro-organisms/Laboratorium voor Microbiologie ("BCCLM") Ghent, Belgium
NBRC: Biological Resource Center (NBRC), Chiba, Japan
NCIMB: National Collections of Industrial, Food and Marine Bacteria, UK
NRRL: USDA ARS, Peoria, IL., USA In certain embodiments, the mono-cultures or co-cultures and resultant fermentation broths and fermentation broth products can comprise one or more *Methylobacterium* isolates or mutants that produce increased levels of useful nutrients or plant growth regulators. U.S. Pat. No. 8,153,118 discloses various *Methylobacterium* isolates that produce increased levels of vitamin B-12 and amino acids that can be used in the methods and compositions provided herein. Fermentation broths, fermentation broth products, and compositions that comprise one or more of the *Methylobacterium* such as *Methylobacterium* mutant B12-11 having accession number ATCC PTA-1561 that overproduces vitamin B-12, *Methylobacterium rhodinum* (ATCC#43282) that over-produces the amino acid threonine, *Methylobacterium* sp. (ATCC#21371) that over-produces the amino acid L-glutamic acid, *Methylobacterium* sp. (ATCC#21372) that over-produces the amino acid L-glutamic acid, *Methylobacterium* sp. (ATCC#21926) over-produces the amino acid L-lysine, *Methylobacterium* sp. (ATCC#21969) over-produces the amino acid L-glutamic acid, *Methylobacterium* sp. (ATCC#21927) over-produces the amino acids L-lysine, L-aspartic acid, L-alanine, L-valine, L-leucine, and L-arginine, and/or *Methylobacterium* sp. (ATCC#21438) that produces single-cell protein are also provided.

In certain embodiments, the fermentation broth, fermentation broth product, or compositions provided herein can further comprise one or more introduced microorganisms of pre-determined identity other than *Methylobacterium*. Other microorganisms that can be added include, but are not limited to, microorganisms that are biopesticidal or provide some other benefit when applied to a plant or plant part. Biopesticidal or otherwise beneficial microorganisms thus include, but are not limited to, various *Bacillus* sp., *Pseudomonas* sp., *Coniothyrium* sp., *Pantoea* sp., *Streptomyces* sp., and *Trichoderma* sp. Microbial biopesticides can be a bacterium, fungus, virus, or protozoan. Particularly useful biopesticidal microorganisms include various *Bacillus subtilis*, *Bacillus thuringiensis*, *Bacillus pumilis*, *Pseudomonas syringae*, *Trichoderma harzianum*, *Trichoderma virens*, and *Streptomyces lydicus* strains. Other microorganisms that are added can be genetically engineered or naturally occurring isolates that are available as pure cultures. In certain embodiments, it is anticipated that the bacterial or fungal microorganism can be provided in the fermentation broth, fermentation broth product, or composition in the form of a spore. Still other microorganisms that can be added include, but are not limited to, microorganisms that are photosynthetic microorganisms. Such photosynthetic organisms include, but are not limited to, algae. Such algae can include, but are not limited to, algae of the genii of *Protococcus, Ulva, Codium, Enteromorpha, Neochloris*, and/or *Chlamydomonas*.

In certain embodiments, the aqueous liquid component of the emulsion used in the culture medium is prepared from inexpensive and readily available components, including, but not limited to, inorganic salts such as potassium phosphate, magnesium sulfate and the like, carbon sources such as glycerol, methanol, glutamic acid, aspartic acid, succinic acid and the like, and amino acid blends such as peptone, tryptone, and the like. Exemplary liquid media that can be used include, but are not limited to, ammonium mineral salts (AMS) medium (Whittenbury et al., 1970), Vogel-Bonner (VB) minimal culture medium (Vogel and Bonner, 1956), and LB broth ("Luria-Bertani Broth").

In certain embodiments, the emulsion comprises an aqueous liquid and a liquid that is not miscible, or only partially miscible, in the aqueous liquid. Non-aqueous liquids that are not miscible, or only partially miscible, in water include, but are not limited to, any of the following: (1) liquids having a miscibility in water that is equal to or less than that of n-pentanol, n-hexanol, or n-heptanol at 25 degrees C.; (2) liquids comprising an alcohol, an aldehyde, a ketone, a fatty acid, a phospholipid, or any combination thereof; (3) alcohols is selected from the group consisting of aliphatic alcohols containing at least 5, 6, or 7 carbons and sterols; (4) an animal oil, microbial oil, synthetic oil, plant oil, or combination thereof; and/or, (5) a plant oil is selected from the group consisting of corn, soybean, cotton, peanut, sunflower, olive, flax, coconut, palm, rapeseed, sesame seed, safflower, and combinations thereof. In certain embodiments, the immiscible or partially immiscible non-aqueous liquid can comprise at least about 0.02% to about 20% of the emulsion by mass. In certain embodiments, the immiscible or partially immiscible non-aqueous liquid can comprise at least about any of about 0.05%, 0.1%, 0.5%, or 1% to about 3%, 5%, 10%, or 20% of the emulsion by mass.

In general, the non-aqueous liquid component used in the emulsions that provide for the efficient growth of *Methylobacterium* can be any non-aqueous liquid which is immiscible or only partially miscible in water or aqueous solutions. Such suitable non-aqueous liquids are also non-bacteriocidal or non-bacteriostatic with respect to *Methylobacterium* when provided in the liquid culture media. In certain embodiments, such suitable non-aqueous liquids are also non-aqueous liquids that are readily obtained in sterile form or rendered sterile. Non-aqueous liquids used herein can be sterilized by any method that provides for removal of contaminating microorganisms and thus include, but, are not limited to, methods such as autoclaving, irradiation, chemical treatment, and any combination thereof.

In certain embodiments, provided herein, a solid substance can be added to the emulsion of the methods, fermentation products, or compositions provided herein. Methods and compositions for growing *Methylobacterium* in biphasic media comprising a liquid and a solid are disclosed in co-assigned U.S. patent application Ser. No. 13/907,161, which is incorporated herein by reference in its entirety, and in co-assigned International Patent Application PCT/US13/43722, which is incorporated herein by reference in its entirety. These solid substances include natural substances of animal, plant, microbial, fungal, or mineral origin, manmade substances, or combinations of natural and manmade substances. In certain embodiments, the solid substances are inanimate solid substances. Inanimate solid substances of animal, plant, microbial, or fungal origin can be obtained from animals, plants, microbes, or fungi that are inviable (i.e. no longer living) or that have been rendered inviable. Diatom shells are thus inanimate solid substances when previously associated diatom algae have been removed or otherwise rendered inviable. Since diatom shells are inanimate solid substances, they are not considered to be photosynthetic organisms or photosynthetic microorganisms. In certain embodiments, solid substances include, but are not limited to, sand, silt, soil, clay, ash, charcoal, diatomaceous earth and other similar minerals, ground glass or glass beads, ground ceramic materials, ceramic beads, bentonite, kaolin, talc, perlite, mica, vermiculite, silicas, quartz powder, montmorillonite, and combinations thereof. In certain embodiments, the solid substance can be a polymer or polymeric beads. Polymers that can be used as a solid substance include, but are not limited to, various polysaccharides such as cellulosic polymers and chitinous polymers which are insoluble or only partially soluble in water or aqueous solutions, agar (i.e. galactans), and combinations thereof. In certain embodiments, the solid substance can be an insoluble or only partially soluble salt crystal. Salt crystals that can be used include, but are not limited to, insoluble or only partially soluble carbonates, chromates, sulfites, phosphates, hydroxides, oxides, and sulfides. In certain embodiments, the solid substance can be a microbial cell, fungal cell, microbial spore, or fungal spore. In certain embodiments, the solid substance can be a microbial cell or microbial spore wherein the microbial cell or microbial spore is not a photosynthetic microorganism. In certain embodiments, the microbial cell or microbial spore is not a photosynthetic microorganism, where the photosynthetic microorganism is selected from the group consisting of algae, cyanobacteria, diatoms, *Botryococcus braunii, Chlorella, Dunaliella tertiolecta, Gracilaria, Pleurochrysis carterae, Sargassum*, and *Ulva*. In still other embodiments, the solid substance can be an inactivated (i.e. inviable) microbial cell, fungal cell, microbial spore, or fungal spore. In still other embodiments, the solid substance can be a quiescent (i.e. viable but not actively dividing) microbial cell, fungal cell, microbial spore, or fungal spore. In still other embodiments, the solid substance can be cellular debris of microbial origin. In still other embodiments, the solid substance can be particulate matter from any part of a plant. Plant parts that can be used to obtain the solid substance include, but are not limited to, cobs, husks, hulls, leaves, roots, flowers, stems, bark, seeds, and combinations thereof. Products obtained from processed plant parts including but not limited to, bagasse, wheat bran, soy grits, crushed seed cake, stover, and the like can also be used. Such plant parts, processed plants, and/or processed plant parts can be milled to obtain the solid material in a particulate form that can be used. In certain embodiments, wood or a wood product including, but not limited to, wood pulp, sawdust, shavings, and the like can be used. In certain embodiments, the solid substance can be a particulate matter from an animal(s), including, but not limited to, bone meal, gelatin, ground or powdered shells, hair, macerated hide, and the like.

In certain embodiments, the solid substance added to the emulsion is provided in a particulate form that provides for distribution of the solid substance in the culture media. In certain embodiments, the solid substance is comprised of particle of about 2 microns to about 1000 microns in average length or average diameter. In certain embodiments, the solid substance is comprised of particle of about 1 microns to about 1000 microns in average length or average diameter. In certain embodiments, the solid substance is a particle of about 1, 2, 4, 10, 20, or 40 microns to any of about 100, 200, 500, 750, or 1000 microns in average length or average diameter. Desirable characteristics of particles used in the methods and compositions provided herein include suitable wettability such that the particles can be suspended throughout the media upon agitation.

In certain embodiments, a liquid or a solid added to an emulsion in the fermentation products, compositions, and methods provided herein is an emulsifier that provides for stabilization of the emulsion. Such emulsifiers can include, but are not limited to, surfactants and thickeners. Surfactants can include, but are not limited to, various ionic or non-ionic detergents including but not limited to, anionic surfactants, cationic surfactants, amphoteric surfactants, organo-silicate surfactants, and/or acidified surfactants. Hydrocolloid polymers used as emulsifiers in the fermentation products, compositions, and methods provided herein include, but are not limited to, agar, alginate, arabinoxylan, carrageenan, carboxymethylcellulose, cellulose, curdlan, gelatin, gellan, β-glucan, guar gum, gum arabic, locust bean gum, pectin, starch, xanthan gum, and mixtures thereof. Other emulsifiers include, but are not limited to, various clays and proteins. Certain agriculturally acceptable excipients and adjuvants disclosed herein and elsewhere can also be used as emulsifiers.

In certain embodiments, the solid substance added to the emulsion is provided in the media, fermentation product, or composition as a colloid wherein the continuous phase is a liquid and the discontinuous phase is the solid. Suitable solids that can be used form colloids in liquid media used to grow *Methylobacterium* include, but are not limited to, various solids that are referred to as hydrocolloids. Such hydrocolloids used in the media, methods and compositions provided herein can be hydrophilic polymers, of plant, animal, microbial, or synthetic origin. Hydrocolloid polymers used in the methods can contain many hydroxyl groups and/or can be polyelectrolytes. Hydrocolloid polymers used in the compositions and methods provided herein include, but are not limited to, agar, alginate, arabinoxylan, carrageenan, carboxymethylcellulose, cellulose, curdlan, gelatin, gellan, β-glucan, guar gum, gum arabic, locust bean gum, pectin, starch, xanthan gum, and mixtures thereof. In certain embodiments, the colloid used in the media, methods, and compositions provided herein can comprise a hydrocolloid polymer and one or more proteins.

In certain embodiments, the solid substance added to the emulsion can be a solid substance that provides for adherent growth of the *Methylobacterium* on the solid substance. *Methylobacterium* that are adhered to a solid substance are *Methylobacterium* that cannot be substantially removed by simply washing the solid substance with the adherent *Methylobacterium* with growth media whereas non-adherent *Methylobacterium* can be substantially removed by washing the solid substance with liquid growth media. In this context, "substantially removed" means that at least about 30%, 40%, 50%, 60%, 70%, or 80% the *Methylobacterium* present are removed when the solid substance is washed with three volumes of liquid growth media. Such washing can be effected by a variety of methods including, but not limited to, decanting liquid from a washed solid phase or passing liquid through a solid phase on a filter that permits flow through of bacteria in the liquid. In certain embodiments, the adherent *Methylobacterium* that are associated with the solid can include both *Methylobacterium* that are directly attached to the solid and/or *Methylobacterium* that are indirectly attached to the solid substance. *Methylobacterium* that are indirectly attached to the solid substance include, but are not limited to, *Methylobacterium* that are attached to another *Methylobacterium* or to another microorganism that is attached to the solid substance, *Methylobacterium* that are attached to the solid substance by being attached to another substance that is attached to the solid substance, and the like. In certain embodiments, at least 10%, 20%, 30%, 40%, 50%, 60%, 70%, 80%, 90%, 95%, 98%, 99%, 99.5% or 99.9% of the *Methylobacterium* in the fermentation broth, fermentation broth product, or compositions are *Methylobacterium* that are adhered to the solid substance. In certain embodiments, adherent *Methylobacterium* can be present on the surface of the solid substance in the fermentation broth, fermentation broth product, or composition at a density of at least about 1 *Methylobacterium*/20 square micrometers, of at least about 1 *Methylobacterium*/10 square micrometers, of at least about 1 *Methylobacterium*/10 square micrometers, of at least about 1 Methylobacterium/5 square micrometers, of at least about 1 *Methylobacterium*/2 square micrometers, or of at least about 1 *Methylobacterium*/square micrometer. In certain embodiments, adherent *Methylobacterium* can be present on the surface of the solid substance in the fermentation broth, fermentation broth product, or composition at a density of at least about 1 *Methylobacterium*/20 square micrometers to about 1 *Methylobacterium*/square micrometer, of at least about 1 *Methylobacterium*/10 square micrometers to about 1 *Methylobacterium*/square micrometer, of at least about 1 *Methylobacterium*/10 square micrometers to about 1 *Methylobacterium*/square micrometer, of at least about 1 *Methylobacterium*/5 square micrometers to about 1 *Methylobacterium*/square micrometer, or of at least about 1 *Methylobacterium*/2 square micrometers to about 1 *Methylobacterium*/square micrometer. In certain embodiments, adherent *Methylobacterium* can be present on the surface of the solid substance in the fermentation broth, fermentation broth product, or composition at a density of at least about 1 *Methylobacterium*/20 square micrometers to about 1 *Methylobacterium*/2 square micrometers, of at least about 1 *Methylobacterium*/10 square micrometers to about 1 *Methylobacterium*/2 square micrometers, of at least about 1 *Methylobacterium*/10 square micrometers to about 1 *Methylobacterium*/2 square micrometers, or of at least about 1 *Methylobacterium*/5 square micrometers to about 1 *Methylobacterium*/2 square micrometers. Fermentation products and broths provided herein can comprise a liquid phase that contains non-adherent *Methylobacterium*. In certain embodiments, titers of non-adherent *Methylobacterium* in the liquid phase can be less than about 100,000, 10,000, or 1,000 CFU/ml.

Culture methods provided can yield fermentation products with *Methylobacterium* at a titer of greater than about $5 \times 10^7$ colony-forming units per milliliter, about $5 \times 10^8$ colony-forming units per milliliter, at a titer of greater than about $1 \times 10^9$ colony-forming units per milliliter, at a titer of greater than about $1 \times 10^{10}$ colony-forming units per milliliter, at a titer of at least about $3 \times 10^{10}$ colony-forming units per milliliter. In certain embodiments, fermentation broths provided herein can comprise *Methylobacterium* at a titer of at least about $5 \times 10^7$ colony-forming units per milliliter to at least about $3 \times 10^{10}$ colony-forming units per milliliter, at least about $5 \times 10^7$ colony-forming units per milliliter to at least about $4 \times 10^{10}$ colony-forming units per milliliter, or at least about $5 \times 10^7$ colony-forming units per milliliter to at least about $6 \times 10^{10}$ colony-forming units per milliliter. In certain embodiments, fermentation broths provided herein can comprise *Methylobacterium* at a titer of at least about $1 \times 10^9$ colony-forming units per milliliter to at least about $3 \times 10^{10}$ colony-forming units per milliliter, at least about $1 \times 10^9$ colony-forming units per milliliter to at least about $4 \times 10^{10}$ colony-forming units per milliliter, or at least about $1 \times 10^9$ colony-forming units per milliliter to at least about $6 \times 10^{10}$ colony-forming units per milliliter. In certain embodiments, fermentation broths provided herein will comprise *Methylobacterium* at a titer of at least about $1 \times 10^{10}$ colony-forming units per milliliter to at least about $3 \times 10^{10}$ colony-forming units per milliliter, at least about $1 \times 10^{10}$ colony-forming units per milliliter to at least about $4 \times 10^{10}$ colony-forming units per milliliter, or at least about $1 \times 10^{10}$ colony-forming units per milliliter to at least about $6 \times 10^{10}$ colony-forming units per milliliter. In certain embodiments, fermentation broths provided herein will comprise *Methylobacterium* at a titer of, at least about $3 \times 10^{10}$ colony-forming units per milliliter to at least about $4 \times 10^{10}$ colony-forming units per milliliter, or at least about $3 \times 10^{10}$ colony-forming units per milliliter to at least about $6 \times 10^{10}$ colony-forming units per milliliter.

Fermentation broths, fermentation broth products, fermentation products, or other compositions comprising emulsions with *Methylobacterium* can be used to make various compositions useful for treating plants or plant parts. Alternatively, fermentation broths, fermentation broth products, fermentation products, or other compositions comprising emulsions with *Methylobacterium* can be can be used to treat plants or plant parts. Plants, plant parts, and, in particular, plant seeds that have been at least partially coated with the fermentation broth products or compositions are thus provided. Also provided are processed plant products that contain the fermentation broth products or compositions. Fermentation broths, fermentation broth products, fermentation products, or other compositions comprising emulsions with *Methylobacterium* are particularly useful for treating plant seeds. Seeds that have been at least partially coated with the fermentation broth products or compositions are thus provided. Also provided are processed seed products, including, but not limited to, meal, flour, feed, and flakes that contain the fermentation broth products or compositions provided herein. In certain embodiments, the processed plant product will be non-regenerable (i.e. will be incapable of developing into a plant). In certain embodiments, the emulsion used in the fermentation product or composition that at least partially coats the plant, plant part, or plant seed or that is contained in the processed plant, plant part, or seed product comprises associated *Methylobacterium* that can be readily identified by comparing a treated and an untreated plant, plant part, plant seed, or processed product thereof.

Fermentation broths, fermentation broth products, fermentation products, or other compositions comprising emulsions with *Methylobacterium* can be used to produce industrial products or recombinant proteins or in bioremediation.

Compositions useful for treating plants or plant parts that comprise emulsions comprising *Methylobacterium* can also comprise an agriculturally acceptable adjuvant or an agriculturally acceptable excipient. An agriculturally acceptable adjuvant or an agriculturally acceptable excipient is typically an ingredient that does not cause undue phytotoxicity or other adverse effects when exposed to a plant or plant part. In certain embodiments, the emulsion can itself be an agriculturally acceptable adjuvant or an agriculturally acceptable excipient so long as it is not bacteriocidal or bacteriostatic to the *Methylobacterium*. In other embodiments, the composition further comprises at least one of an agriculturally acceptable adjuvant or an agriculturally acceptable excipient. Any of the aforementioned compositions can also further comprise a pesticide. Pesticides used in the composition include, but are not limited to, an insecticide, a fungicide, a nematocide, and a bacteriocide. In certain embodiments, the pesticide used in the composition is a pesticide that does not substantially inhibit growth of the *Methylobacterium*. As *Methylobacterium* are gram negative bacteria, suitable bacteriocides used in the compositions can include, but are not limited to, bacteriocides that exhibit activity against gram positive bacteria but not gram negative bacteria. Compositions provided herein can also comprise a bacteriostatic agent that does not substantially inhibit growth of the *Methylobacterium*. Bacteriostatic agents suitable for use in compositions provided herein include, but are not limited to, those that exhibit activity against gram positive bacteria but not gram negative bacteria. Any of the aforementioned compositions can also be an essentially dry product (i.e. having about 5% or less water content), a mixture of the composition with an emulsion, or a suspension.

Agriculturally acceptable adjuvants used in the compositions include, but are not limited to, components that enhance product efficacy and/or products that enhance ease of product application. Adjuvants that enhance product efficacy can include various wetters/spreaders that promote adhesion to and spreading of the composition on plant parts, stickers that promote adhesion to the plant part, penetrants that can promote contact of the active agent with interior tissues, extenders that increase the half-life of the active agent by inhibiting environmental degradation, and humectants that increase the density or drying time of sprayed compositions. Wetters/spreaders used in the compositions can include, but are not limited to, non-ionic surfactants, anionic surfactants, cationic surfactants, amphoteric surfactants, organo-silicate surfactants, and/or acidified surfactants. Stickers used in the compositions can include, but are not limited to, latex-based substances, terpene/pinolene, and pyrrolidone-based substances. Penetrants can include mineral oil, vegetable oil, esterified vegetable oil, organo-silicate surfactants, and acidified surfactants. Extenders used in the compositions can include, but are not limited to, ammonium sulphate, or menthene-based substances. Humectants used in the compositions can include, but are not limited to, glycerol, propylene glycol, and diethyl glycol. Adjuvants that improve ease of product application include, but are not limited to, acidifying/buffering agents, anti-foaming/de-foaming agents, compatibility agents, drift-reducing agents, dyes, and water conditioners. Anti-foaming/de-foaming agents used in the compositions can include, but are not limited to, dimethopolysiloxane. Compatibility agents used in the compositions can include, but are not limited to, ammonium sulphate. Drift-reducing agents used in the compositions can include, but are not limited to, polyacrylamides, and polysaccharides. Water conditioners used in the compositions can include, but are not limited to, ammonium sulphate.

Methods of treating plants and/or plant parts with the fermentation broths, fermentation broth products, and compositions are also provided herein. Treated plants, and treated plant parts obtained therefrom, include, but are not limited to, corn, *Brassica* sp. (e.g., *B. napus, B. rapa, B. juncea*), alfalfa, rice, rye, sorghum, millet (e.g., pearl millet (*Pennisetum glaucum*), proso millet (*Panicum miliaceum*), foxtail millet (*Setaria Italica*), finger millet (*Eleusine coracana*)), sunflower, safflower, soybean, tobacco, potato, peanuts, cotton, sweet potato (*Ipomoea batatus*), cassava, coffee, coconut, pineapple, citrus trees, cocoa, tea, banana, avocado, fig, guava, mango, olive, papaya, cashew, macadamia, almond, sugar beets, sugarcane, oats, barley, tomatoes lettuce, green beans, lima beans, peas, cucurbits such as cucumber, cantaloupe, and musk melon, ornamentals, and conifers. Plant parts that are treated include, but are not limited to, leaves, stems, flowers, roots, seeds, fruit, tubers, coleoptiles, and the like. Ornamental plants and plant parts that can be treated include, but are not limited to azalea, hydrangea, hibiscus, roses, tulips, daffodils, petunias, carnation, poinsettia, and chrysanthemum. Conifer plants and plant parts that can be treated include, but are not limited to, pines such as loblolly pine, slash pine, ponderosa pine, lodgepole pine, and Monterey pine; Douglas-fir; Western hemlock; Sitka spruce; redwood; true firs such as silver fir and balsam fir; and cedars such as Western red cedar and Alaska yellow-cedar. Turfgrass plants and plant parts that can be treated include, but are not limited to, annual bluegrass, annual ryegrass, Canada bluegrass, fescue, bentgrass, wheatgrass, Kentucky bluegrass, orchard grass, ryegrass, redtop, Bermuda grass, St. Augustine grass, and zoysia grass. Seeds or other propagules of any of the aforementioned plants can be treated with the fermentation broths, fermentation broth products, fermentation products, and/or compositions provided herein.

In certain embodiments, plants and/or plant parts are treated by applying the fermentation broths, fermentation broth products, fermentation products, and compositions as a spray. Such spray applications include, but are not limited to, treatments of a single plant part or any combination of plant parts. Spraying can be achieved with any device that will distribute the fermentation broths, fermentation broth products, fermentation products, and compositions to the plant and/or plant part(s). Useful spray devices include a boom sprayer, a hand or backpack sprayer, crop dusters (i.e. aerial spraying), and the like. Spraying devices and or methods providing for application of the fermentation broths, fermentation broth products, fermentation products, and compositions to either one or both of the adaxial surface and/or abaxial surface can also be used. Plants and/or plant parts that are at least partially coated with any of a fermentation broth, a fermentation broth product, fermentation product, or compositions that comprise an emulsion with *Methylobacterium* are also provided herein. Also provided herein are processed plant products that comprise a solid substance with *Methylobacterium* adhered thereto.

In certain embodiments, seeds are treated by exposing the seeds to the fermentation broths, fermentation broth products, fermentation products, and compositions that comprise the emulsions provided herein. Seeds can be treated with the fermentation broths, fermentation broth products, and compositions provided herein by methods including, but not limited to, imbibition, coating, spraying, and the like. Seed treatments can be effected with both continuous and/or a batch seed treaters. In certain embodiments, the coated seeds may be prepared by slurrying seeds with a coating composition containing a fermentation broth, fermentation broth product, or compositions provided that comprise the emulsion with *Methylobacterium* and air drying the resulting product. Air drying can be accomplished at any temperature that is not deleterious to the seed or the *Methylobacterium*, but will typically not be greater than 30 degrees Centigrade. The proportion of coating that comprises an emulsion and *Methylobacterium* includes, but is not limited to, a range of 0.1 to 25% by weight of the seed, 0.5 to 5% by weight of the seed, and 0.5 to 2.5% by weight of seed. In certain embodiments, an emulsion that further comprises a solid substance used in the seed coating or treatment will have *Methylobacterium* adhered thereon. In certain embodiments, an emulsion that further comprises a solid substance used in the seed coating or treatment will be associated with *Methylobacterium* and will be a fermentation broth, fermentation broth product, or composition obtained by the methods provided herein. Various seed treatment compositions and methods for seed treatment disclosed in U.S. Pat. Nos. 5,106,648, 5,512,069, and 8,181,388 are incorporated herein by reference in their entireties and can be adapted for use with an active agent comprising the fermentation broths, fermentation broth products, or compositions provided herein. In certain embodiments, the composition used to treat the seed can contain agriculturally acceptable excipients that include, but are not limited to, woodflours, clays, activated carbon, diatomaceous earth, fine-grain inorganic solids, calcium carbonate and the like. Clays and inorganic solids that can be used with the fermentation broths, fermentation broth products, or compositions provided herein include, but are not limited to, calcium bentonite, kaolin, china clay, talc, perlite, mica, vermiculite, silicas, quartz powder, montmorillonite and mixtures thereof. Agriculturally acceptable adjuvants that promote sticking to the seed that can be used include, but are not limited to, polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxy methylcelluloses, hydroxypropylcellulose, hydroxymethylpropylcelluloses, polyvinyl pyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethylcellulose, chitosan, polyethylene oxide, acrylimide polymers and copolymers, polyhydroxyethyl acrylate, methylacrylimide monomers, alginate, ethylcellulose, polychloroprene and syrups or mixtures thereof. Other useful agriculturally acceptable adjuvants that can promote coating include, but are not limited to, polymers and copolymers of vinyl acetate, polyvinylpyrrolidone-vinyl acetate copolymer and water-soluble waxes. Various surfactants, dispersants, anticaking-agents, foam-control agents, and dyes disclosed herein and in U.S. Pat. No. 8,181,388 can be adapted for use with an active agent comprising the fermentation broths, fermentation broth products, or compositions provided herein.

EXAMPLES

The following examples are included to demonstrate preferred embodiments of the invention. It will be appreciated by those of skill in the art that the techniques disclosed in the following examples represent techniques discovered by the Applicants to function well in the practice of the invention, and thus can be considered to constitute preferred modes for its practice. However, those of skill in the art should, in light of the instant disclosure, appreciate that many changes can be made in the specific embodiments that are disclosed, while still obtaining like or similar results, without departing from the scope of the invention.

Example 1. Growth of PPFM Bacteria on Solid Agar Plate Media

For the growth of PPFM bacteria on solid agar plate media, a variety of standard media were tested.

One medium used was ammonium mineral salts (AMS) medium (Whittenbury et al., 1970). AMS medium contains, per liter, 700 milligrams of dibasic potassium phosphate anhydrous, 540 milligrams of monobasic potassium phosphate anhydrous, one gram of magnesium sulfate heptahydrate, 500 milligrams of ammonium chloride anhydrous, 200 milligrams of calcium chloride dehydrate, 4 milligrams of ferric sulfate heptahydrate, 100 micrograms of zinc sulfate heptahydrate, 30 micrograms of manganese chloride tetrahydrate, 300 micrograms of boric acid anhydrous, 200 micrograms of cobalt chloride hexahydrate, 10 micrograms of copper chloride dehydrate, 20 micrograms of nickel chloride hexahydrate, and 60 micrograms of sodium molybdate dehydrate.

AMS medium was prepared from four stock solutions, listed below.

| Stock solution I: for one liter at 50X concentration | |
|---|---|
| dibasic potassium phosphate, anhydrous | 35 grams |
| monobasic potassium phosphate, anhydrous | 27 grams |

| Stock solution II: for one liter at 50X concentration | |
|---|---|
| magnesium sulfate heptahydrate | 50 grams |
| ammonium chloride, anhydrous | 25 grams |

| Stock solution III: for one liter at 50X concentration | |
|---|---|
| calcium chloride dihydrate | 10 grams |

| Trace metals stock solution: for one liter at 1000X concentration | |
|---|---|
| ferric sulfate heptahydrate | 4 grams |
| zinc sulfate heptahydrate | 100 milligrams |
| manganese chloride tetrahydrate | 30 milligrams |
| boric acid, anhydrous | 300 milligrams |
| cobalt chloride hexahydrate | 200 milligrams |
| copper chloride dihydrate | 10 milligrams |
| nickel chloride hexahydrate | 20 milligrams |
| sodium molybdate dihydrate | 60 milligrams |

Stock solutions I, II, and III were autoclaved separately. The trace metals stock solution could not be autoclaved, as most of the salts precipitated out during the autoclaving step, and so it was filter-sterilized through a 0.2 micrometer filter apparatus. These steps were necessary to insure the preparation of a water-clear AMS culture medium with all ingredients in solution. As originally described by Whittenbury et al. (1970), the phosphate-containing components of the AMS medium were segregated from the other components until the final finishing steps of the medium preparation, preventing the formation of insoluble magnesium phosphate and calcium phosphate crystals.

To prepare one liter of solid agar plate media with an AMS base, 15 grams of agar were added to 940 ml of distilled water, and this mixture was autoclaved. After autoclaving, 20 ml each of stock solutions I, II, and III were added, along with one ml of the filter-sterilized trace metals stock solution.

If other medium components, such as a carbon source, were to be incorporated, for the most part these were added to the water and agar mixture before autoclaving. The one exception to this was methanol, which was filter-sterilized through a 0.2 micrometer filter apparatus and added after the base medium had been autoclaved.

A second medium used was Vogel-Bonner (VB) minimal culture medium (Vogel and Bonner, 1956). VB medium contains, per liter, 298 milligrams of magnesium sulfate heptahydrate, 14.93 grams of anhydrous dibasic potassium phosphate, 5.22 grams of sodium ammonium phosphate tetrahydrate, and 2.73 grams of anhydrous citric acid (the free acid form).

Vogel-Bonner minimal medium was prepared from a 25× stock solution of the salts and citric acid. This 25× stock solution was prepared by dissolving in one liter of distilled water the following amounts of each ingredient, in the order listed, and making sure each one was completely dissolved before adding the next one: 7.46 grams of magnesium sulfate heptahydrate, 68.23 grams of anhydrous citric acid, 373.13 grams of anhydrous dibasic potassium phosphate, and 130.60 grams of sodium ammonium phosphate tetrahydrate. By first dissolving the magnesium sulfate and then adding the citric acid, the magnesium ions were chelated by the citrate ions, preventing the formation of insoluble magnesium phosphate crystals when the phosphate salts are added. This insured the preparation of a water-clear culture medium with all ingredients in solution.

To prepare one liter of solid agar plate media with a VB base, 15 grams of agar were added to 960 ml of distilled water and this mixture was autoclaved. After autoclaving, 40 ml of the 25× VB salts stock solution were added.

If other medium components, such as a carbon source, were to be incorporated, for the most part these were added to the water and agar mixture before autoclaving. The one exception to this was methanol, which was filter-sterilized through a 0.2 micrometer filter apparatus and added after the base medium had been autoclaved.

A third medium used was LB broth. LB broth contains, per liter, 10 grams of tryptone, 5 grams of yeast extract, and 10 grams of sodium chloride. All components were dissolved in one liter of distilled water and autoclaved. This medium was water-clear, with all ingredients in solution.

To prepare one liter of solid agar plate media with an LB base, 15 grams of agar were added to one liter of LB broth, and this mixture was autoclaved.

Corpe and Basile (1982) conducted a systematic survey of the growth of various strains of PPFM bacteria in AMS media containing various carbon sources. Many of the tested substances supported little to no growth of PPFM bacteria. Corpe and Basile reported that glycerol and glutamate were relatively good carbon sources for PPFM bacteria, and that methanol, glucose, aspartate, succinate and malate were intermediate as carbon sources for PPFM bacteria.

The Applicants measured the growth of *Methylobacterium extorquens* on LB plates, as well as on AMS and VB plates supplemented with various carbon sources. The carbon sources, listed below, were all added to the AMS or VB base salts media at 10 grams per liter. In addition, some media compositions were tested that included peptone at 10 grams per liter. The *Methylobacterium extorquens* was streaked out on the various agar plates, and they were incubated at 30 degrees C. for up to two weeks. Growth was measured as the number of days of incubation required for the colonies to become full-sized (about 2 millimeters in diameter); for those growth conditions where full-sized colonies did not form even after prolonged incubation, the colonies were scored as medium-sized (about 1 millimeters in diameter) or small-sized (about 0.5 millimeters in diameter or smaller). All of the colonies observed were of a deep, saturated pink color, as is characteristic of PPFM bacteria.

The results were as follows:

| | |
|---|---|
| VB plus aspartate | small-sized in 9 days |
| VB plus succinate | small-sized in 10 days |
| VB plus malate | small-sized in 10 days |
| LB | full-sized in 9 days |
| AMS plus glucose | full-sized in 9 days |
| VB plus glucose | full-sized in 14 days |
| AMS plus methanol | full-sized in 6 days |
| VB plus methanol | medium-sized in 10 days |
| AMS plus glutamate and peptone | full-sized in 5 days |
| AMS plus glycerol and peptone | full-sized in 5 days |
| VB plus glycerol and peptone | full-sized in 6 days |

The fastest and most abundant growth of the PPFM bacterium *Methylobacterium extorquens* on the tested solid agar plate media was on AMS plus glycerol and peptone or AMS plus glutamate and peptone, followed closely by AMS plus methanol or VB plus glycerol and peptone. Growth on the other tested media was significantly slower.

Example 2. Growth of PPFM Bacteria in Clear, Monophasic Liquid Media

For those four solid agar plate media found in Example 1 to have supported the fastest and most abundant growth of the PPFM bacterium *Methylobacterium extorquens*, the corresponding liquid versions (that is, no added agar) were prepared and tested. These four liquid media, prepared as described in Example 1 (with the sole exception being that they did not contain any agar) were all water-clear liquids, with all ingredients in solution.

To flasks containing 100 milliliters of these four liquid media, an inoculum of the PPFM bacterium *Methylobacterium extorquens* was added to give an initial titer of about $1 \times 10^5$ colony-forming units (CFU) per milliliter. The flasks were placed on a rotary shaker incubator set and grown for 5 days at 30 degrees C. and 250 rpm. At the end of the 5 days of incubation, the titers of PPFM bacteria in the flasks were determined. The results were:

| liquid medium | initial titer of PPFM | titer of PPFM after 5 days |
|---|---|---|
| AMS plus glycerol and peptone | $1.4 \times 10^5$ | $4.5 \times 10^5$ |
| AMS plus glutamate and peptone | $2.0 \times 10^5$ | $3.8 \times 10^5$ |
| AMS plus methanol | $1.1 \times 10^5$ | $2.1 \times 10^5$ |
| VB plus glycerol and peptone | $1.7 \times 10^5$ | $1.3 \times 10^5$ |

A striking aspect of these results is the very poor growth of the PPFM bacteria in all of these water-clear liquid media, in the presence of the exact same nutrients as were present in the solid agar plate forms of these media on which the PPFM bacteria grew rapidly and abundantly (as described in Example 1). Indeed, in all of these flasks, there was little or no visible turbidity (the classical indication of microbial growth) and no hint of a pink hue whatsoever.

Example 3. Growth of PPFM Bacteria in a Biphasic Culture Media Containing Insoluble Salt Crystals For the preparation of the biphasic culture media, liquid AMS plus glycerol and peptone medium was made turbid (i.e. provided with a solid substance) by deliberately forming insoluble crystals of magnesium phosphate and/or calcium phosphate. To deliberately form insoluble crystals in the media, the preparation method described in Example 1 was altered as follows. All components except the trace metals stock solution were mixed together before autoclaving. That is, to 940 ml of distilled water were added 20 ml each of stock solutions I, II, and III, along with 10 grams of glycerol and 10 grams of peptone. After autoclaving, the medium was completed by the addition of one ml of filter-sterilized trace metals stock solution. The autoclaving of the components of stock solutions I, II, and III, mixed together before autoclaving, resulted in the formation of insoluble salt crystals, presumably primarily magnesium phosphate dibasic and/or calcium phosphate dibasic. After autoclaving, the AMS plus glycerol and peptone medium made by this preparation method yielded a liquid medium that was very turbid with these salt crystals. This new liquid medium was designated "turbid AMS plus glycerol and peptone".

To a flask containing 100 milliliters of the turbid AMS plus glycerol and peptone, an inoculum of the PPFM bacterium *Methylobacterium extorquens* was added to give an initial titer of about $1 \times 10^5$ colony-forming units (CFU) per milliliter. The flask was placed on a rotary shaker incubator set and grown for 3 days at 30 degrees C. and 250 rpm. After just two days, the flask had developed a deep, saturated pink turbidity, indicating fast and abundant growth of PPFM bacteria. At both 2 days and 3 days after inoculation, the titers of PPFM bacteria in the flask were determined. The results were:

| liquid medium | initial titer of PPFM | titer of PPFM after 2 days | titer of PPFM after 3 days |
|---|---|---|---|
| turbid AMS plus glycerol and peptone | $1.7 \times 10^5$ | $1.3 \times 10^8$ | $1.7 \times 10^9$ |

Two striking aspects of this result were the very fast growth of the PPFM bacteria, and their growth to titers approaching 10,000-fold higher than achieved in clear AMS plus glycerol and peptone liquid medium (as shown in Example 2).

Example 4. Growth of PPFM Bacteria in Liquid Media Containing Diatomaceous Earth To test whether diatomaceous earth would be effective at promoting the fast and abundant growth of PPFM bacteria, small amounts of diatomaceous earth were added to AMS plus glycerol and peptone liquid medium. This liquid medium was prepared as described in Example 1, that is, by the preparation method designed to prevent the formation of insoluble salt crystals of magnesium phosphate and calcium phosphate. The diatomaceous earth was added to the water before autoclaving. The amounts of diatomaceous tested were, per liter, 500 milligrams, 1 gram, 1.5 grams, and 2 grams. These new liquid media were designated "AMS plus glycerol and peptone and diatomaceous earth".

To flasks containing 100 milliliters of the AMS plus glycerol and peptone and diatomaceous earth, an inoculum of the PPFM bacterium *Methylobacterium extorquens* was added to give an initial titer of about $1 \times 10^5$ colony-forming units (CFU) per milliliter. The flasks were placed on a rotary shaker incubator set and grown for 3 days at 30 degrees C. and 250 rpm. After just two days, the flasks had all developed a deep, saturated pink turbidity, indicating fast and abundant growth of PPFM bacteria. At both 2 days and 3 days after inoculation, the titers of PPFM bacteria in the flasks were determined. The results were:

| liquid medium | initial titer of PPFM | titer of PPFM after 2 days | titer of PPFM after 3 days |
|---|---|---|---|
| AMS plus glycerol and peptone and 500 mg diatomaceous earth | $1.0 \times 10^5$ | $1.8 \times 10^8$ | $1.1 \times 10^9$ |
| AMS plus glycerol and peptone and 1 gram diatomaceous earth | $1.8 \times 10^5$ | $3.0 \times 10^8$ | $8.4 \times 10^8$ |
| AMS plus glycerol and peptone and 1.5 grams diatomaceous earth | $1.4 \times 10^5$ | $4.0 \times 10^8$ | $1.7 \times 10^9$ |
| AMS plus glycerol and peptone and 2 grams diatomaceous earth | $1.7 \times 10^5$ | $3.4 \times 10^8$ | $2.0 \times 10^9$ |

Two striking aspects of this result are the very fast growth of the PPFM bacteria, and their growth to titers approaching 10,000-fold higher than achieved in clear AMS plus glycerol and peptone liquid medium (as shown in Example 2). The data acquired after 2 days of growth also indicate that increased amounts of growth are correlated to increased amounts of agar within the range of 0.5 grams to 1.5 grams per 100 ml of culture.

Example 5. Titers of Various *Methylobacterium* in the Presence and Absence of Various Solids in the Media Fourteen strains in the genus *Methylobacterium* were purchased from the DSMZ (Braunschweig, Germany) and the ATCC (Manassas, Va., USA). These 14 strains consist of 12 different species, as there were three *M. extorquens* in the set:
1. DSM-6343 *Methylobacterium* extorquens
2. DSM-1819 *Methylobacterium* radiotolerans
3. DSM-13060 *Methylobacterium* extorquens
4. DSM-18172 *Methylobacterium* organophilum
5. DSM-1708 *Methylobacterium* mesophilicum
6. DSM-18207 *Methylobacterium* oryzae
7. DSM-19779 *Methylobacterium* phyllosphaerae
8. ATCC-14718 *Methylobacterium* extorquens
9. ATCC-14821 *Methylobacterium* rhodinum
10. ATCC-21611 *Methylobacterium* rhodesianum
11. ATCC-35065 *Methylobacterium* fujisawaense
12. ATCC-43883 *Methylobacterium* zatmanii
13. ATCC-51358 *Methylobacterium* aminovorans
14. ATCC-700647 *Methylobacterium* thiocyanatum For the tests below, the inocula came from cultures grown in water-clear AMS-GP medium. These cultures were grown in 200 ml of the water-clear AMS-GP medium, titered, and then concentrated ten-fold. These PPFM cultures, with no solid substrates present, were used to inoculate test tubes containing 10 ml of water-clear AMS-GP medium, or AMS-GP medium with various added solid substrates. 20 mg of the various solid substrates were added to each 10 ml tube, yielding a solid substrate concentration equivalent to 2 grams per liter. The target initial titer in each tube was about $1 \times 10^5$ PPFM cells per ml. The inoculated test tubes were placed on a rotary shaker set and grown for three days at 30 degrees C. and 250 rpm. After three days of growth, the PPFM cultures were titered.

Growth of PPFM Strains in Water-Clear AMS-GP Liquid Medium

| | | initial titer | titer after 3 days (CFU/mL) |
|---|---|---|---|
| DSM-6343 | *M. extorquens* | $3.5 \times 10^5$ | $1.2 \times 10^6$ |
| DSM-1819 | *M. radiotolerans* | $1.8 \times 10^5$ | $1.3 \times 10^6$ |
| DSM-13060 | *M. extorquens* | $3.1 \times 10^5$ | $3.2 \times 10^5$ |
| DSM-18172 | *M. organophilum* | $1.4 \times 10^5$ | $1.8 \times 10^5$ |
| DSM-1708 | *M. mesophilicum* | $3.3 \times 10^5$ | $1.0 \times 10^5$ |
| DSM-18207 | *M. oryzae* | $1.1 \times 10^5$ | $2.2 \times 10^5$ |
| DSM-19779 | *M. phyllosphaerae* | $2.1 \times 10^5$ | $1.1 \times 10^6$ |
| ATCC-14718 | *M. extorquens* | $2.0 \times 10^5$ | $1.7 \times 10^5$ |
| ATCC-14821 | *M. rhodinum* | $4.4 \times 10^5$ | $2.9 \times 10^5$ |
| ATCC-21611 | *M. rhodesianum* | $1.8 \times 10^5$ | $1.4 \times 10^5$ |
| ATCC-35065 | *M. fujisawaense* | $1.3 \times 10^5$ | $1.9 \times 10^6$ |
| ATCC-43883 | *M. zatmanii* | $5.0 \times 10^5$ | $1.9 \times 10^5$ |
| ATCC-51358 | *M. aminovorans* | $9.5 \times 10^4$ | $1.7 \times 10^5$ |
| ATCC-700647 | *M. thiocyanatum* | $1.8 \times 10^5$ | $7.6 \times 10^4$ |

Growth of PPFM Strains in Turbid AMS-GP Liquid Medium Containing Insoluble Salt Crystals

| | | initial titer | titer after 3 days (CFU/mL) |
|---|---|---|---|
| DSM-6343 | *M. extorquens* | $2.5 \times 10^5$ | $2.1 \times 10^9$ |
| DSM-1819 | *M. radiotolerans* | $7.6 \times 10^4$ | $6.8 \times 10^8$ |
| DSM-13060 | *M. extorquens* | $1.9 \times 10^5$ | $4.4 \times 10^8$ |
| DSM-18172 | *M. organophilum* | $1.1 \times 10^5$ | $1.9 \times 10^9$ |
| DSM-1708 | *M. mesophilicum* | $1.4 \times 10^5$ | $9.3 \times 10^8$ |
| DSM-18207 | *M. oryzae* | $7.3 \times 10^4$ | $2.4 \times 10^8$ |
| DSM-19779 | *M. phyllosphaerae* | $1.8 \times 10^5$ | $7.5 \times 10^8$ |
| ATCC-14718 | *M. extorquens* | $9.3 \times 10^4$ | $2.0 \times 10^9$ |
| ATCC-14821 | *M. rhodinum* | $7.1 \times 10^4$ | $7.2 \times 10^8$ |
| ATCC-21611 | *M. rhodesianum* | $3.9 \times 10^5$ | $6.8 \times 10^8$ |
| ATCC-35065 | *M. fujisawaense* | $8.2 \times 10^4$ | $2.3 \times 10^8$ |
| ATCC-43883 | *M. zatmanii* | $1.8 \times 10^5$ | $6.2 \times 10^8$ |
| ATCC-51358 | *M. aminovorans* | $6.8 \times 10^4$ | $1.7 \times 10^9$ |
| ATCC-700647 | *M. thiocyanatum* | $4.3 \times 10^5$ | $6.5 \times 10^8$ |

Example 6. Growth of *Methylobacterium* in an Emulsion

Ten *Methylobacterium* PPFM strains were grown in 200 ml of the water-clear AMS-GP medium, titered, and then concentrated ten-fold. These PPFM cultures, with no solid substrates present, were used to inoculate test tubes containing 10 ml of water-clear AMS-GP medium comprising an emulsion made with water-clear AMS-FP medium and an oil. For the emulsions, the oils were added at a concentration equivalent to 20 milliliters per liter. The target initial titer in each tube was about $1 \times 10^5$ PPFM colony forming units per ml.

To prepare the emulsions, two sterile 60 milliliter luer lock syringes were attached to a sterile 3-way luer lock stopcock (catalog number S7521, of Sigma-Aldrich Co., St. Louis, Mo.). One syringe was empty, and the other contained 49 milliliters of sterile water-clear AMS-GP liquid medium and one milliliter of sterile oil. The liquid was forcefully pushed back and forth between the two syringes. This forcible mixing through the small orifice of the stopcock produced an emulsion of the two liquids.

The inoculated test tubes were placed on a rotary shaker set and grown for three days at 30 degrees C. and 250 rpm.

a. Growth of PPFM Strains in AMS-GP Liquid Medium Made into an Emulsion with Sesame Oil (at 20 Milliliters Per Liter)

| | | initial titer | titer after 3 days (CFU/mL) |
|---|---|---|---|
| DSM-6343 | *M. extorquens* | $3.2 \times 10^5$ | $2.2 \times 10^8$ |
| DSM-1819 | *M. radiotolerans* | $8.2 \times 10^4$ | $9.1 \times 10^7$ |
| DSM-13060 | *M. extorquens* | $2.9 \times 10^5$ | $1.5 \times 10^8$ |
| DSM-18207 | *M. oryzae* | $1.4 \times 10^5$ | $2.9 \times 10^8$ |
| DSM-19779 | *M. phyllosphaerae* | $3.5 \times 10^5$ | $1.0 \times 10^8$ |
| ATCC-14718 | *M. extorquens* | $8.4 \times 10^4$ | $2.5 \times 10^8$ |
| ATCC-21611 | *M. rhodesianum* | $2.3 \times 10^5$ | $3.5 \times 10^8$ |
| ATCC-35065 | *M. fujisawaense* | $6.7 \times 10^4$ | $8.6 \times 10^7$ |
| ATCC-51358 | *M. aminovorans* | $5.7 \times 10^4$ | $2.7 \times 10^8$ |
| ATCC-700647 | *M. thiocyanatum* | $8.6 \times 10^4$ | $8.6 \times 10^7$ |

After three days of growth, the emulsions were a rich pink in color, indicating that the PPFMs had grown well in the emulsion. These were vortexed vigorously, and then titered. The titers of PPFM cells attained were higher than those attained by growing the PPFM in clear AMS-GP liquid medium (see representative results of Example 5 where PPFM grown for 3 days in water clear AMS-GP media did not exceed $10^6$ colony forming units per ml).

b. Growth of PPFM Strains in AMS-GP Liquid Medium Made into an Emulsion with Coconut Oil (at 20 Milliliters Per Liter)

| | | initial titer | titer after 3 days (CFU/mL) |
|---|---|---|---|
| DSM-6343 | *M. extorquens* | $5.7 \times 10^4$ | $4.6 \times 10^8$ |
| DSM-1819 | *M. radiotolerans* | $9.3 \times 10^4$ | $5.5 \times 10^7$ |
| DSM-13060 | *M. extorquens* | $8.5 \times 10^4$ | $3.7 \times 10^8$ |
| DSM-18207 | *M. oryzae* | $2.5 \times 10^5$ | $7.8 \times 10^7$ |
| DSM-19779 | *M. phyllosphaerae* | $1.4 \times 10^5$ | $5.7 \times 10^8$ |
| ATCC-14718 | *M. extorquens* | $3.0 \times 10^5$ | $7.1 \times 10^7$ |
| ATCC-21611 | *M. rhodesianum* | $6.8 \times 10^4$ | $9.3 \times 10^7$ |
| ATCC-35065 | *M. fujisawaense* | $8.9 \times 10^4$ | $4.5 \times 10^8$ |
| ATCC-51358 | *M. aminovorans* | $8.0 \times 10^4$ | $9.4 \times 10^7$ |
| ATCC-700647 | *M. thiocyanatum* | $7.5 \times 10^4$ | $4.7 \times 10^8$ |

After three days of growth, the emulsions were a rich pink in color indicating that the PPFMs had grown well in the emulsion. These were vortexed vigorously, and then titered. The titers of PPFM cells attained were higher than those attained by growing the PPFM in clear AMS-GP liquid medium (see representative results of Example 10 where PPFM grown for 3 days in water clear AMS-GP media did not exceed $10^6$ colony forming units per ml).

Example 7. Growth of PPFM Bacteria in a Controlled Bioreactor

The growth of bacteria in flasks, incubated on a rotary shaker, is limited by changes in pH brought about by the metabolism of the carbon source(s) in the growth medium. Controlled bioreactors (also known as "fermenters" or "fermentation vessels") avoid this limitation by maintaining the pH at the desired level through the controlled addition of acids or bases, as appropriate. Another factor which can limit the growth of bacteria is the availability of dissolved oxygen. Controlled bioreactors avoid this limitation by maintaining adequate levels of dissolved oxygen through the controlled adjustment of airflow into the reactor vessel, the agitation rate of the vessel, and the air pressure within the vessel.

When grown in a controlled bioreactor containing the AMS plus glycerol and peptone liquid medium described in Example 1, further supplemented with a second immiscible liquid to form an emulsion by any of the methods disclosed or claimed herein, or as described in the preceding Example 6, the final titer of PPFM bacteria achieved will be at least about 10- or at least about 30-fold higher than that achieved in flasks.

Example 8. Plant Seed or Foliar Treatment Compositions Comprising Emulsions with *Methylobacterium*

To obtain compositions suitable for plant seed or foliar treatments, *Methylobacterium* are cultured in an emulsion by any of the methods disclosed or claimed herein, or as described in the preceding Example 6. Typically, the *Methylobacterium* are cultured to a high titer (i.e. at least about $5\times10^7$ colony-forming units per mL). *Methylobacterium* in the emulsion are then harvested. Harvesting can be achieved by filtration, centrifugation, decanting, and combinations thereof. Harvested material can be applied directly to seeds or plants in certain instances. In other instances, the harvested material is dried by lyophilization or spray drying and the like prior to application. Dried material can also be reconstituted with liquids as necessary or desired prior to application to plants or seed. It is also possible to add additional agriculturally acceptable excipients and/or adjuvants to any of the fermentation broth comprising the emulsion containing *Methylobacterium* or to the harvested *Methylobacterium*. Added excipients can include woodflours, clays, activated carbon, diatomaceous earth, fine-grain inorganic solids, calcium carbonate and the like. Clays and inorganic solids that can be added as excipients in the compositions include calcium bentonite, kaolin, china clay, talc, perlite, mica, vermiculite, silicas, quartz powder, montmorillonite and mixtures thereof. Agriculturally acceptable adjuvants that promote sticking to the seed or other plant parts that can be added to the compositions include polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxy methylcelluloses, hydroxypropylcellulose, hydroxymethylpropylcelluloses, polyvinyl pyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethylcellulose, chitosan, polyethylene oxide, acrylimide polymers and copolymers, polyhydroxyethyl acrylate, methylacrylimide monomers, alginate, ethylcellulose, polychloroprene and syrups or mixtures thereof. Other useful agriculturally acceptable adjuvants that can promote coating of seeds or other plant parts include polymers and copolymers of vinyl acetate, polyvinylpyrrolidone-vinyl acetate copolymer and water-soluble waxes. These compositions can be maintained in a dry or semi dry form or can be formulated into slurries by addition of liquids as desired. The compositions can then be used to spray or coat the plants or seeds to obtain beneficial effects associated with application of *Methylobacterium* to plants.

REFERENCES

Abanda-Nkpwatt, D., M. Musch, J. Tschiersch, M. Boettner, and W. Schwab. 2006. Molecular interaction between *Methylobacterium extorquens* and seedlings: growth promotion, methanol consumption, and localization of the methanol emission site. J. Exp. Bot. 57: 4025-4032.

Cao, Y-R, Wang, Q., Jin, R-X., Tang, S-K., He, W-X., Lai, H-X, Xu, L-H., and C-L Jiang. 2011. *Methylobacterium soli* sp. nov. a methanol-utilizing bacterium isolated from the forest soil. Antonie van Leeuwenhoek (2011) 99:629-634.

Corpe, W. A., and D. V. Basile. 1982. Methanol-utilizing bacteria associated with green plants. Devel. Industr. Microbiol. 23: 483-493.

Corpe, W. A., and S. Rheem. 1989. Ecology of the methylotrophic bacteria on living leaf surfaces. FEMS Microbiol. Ecol. 62: 243-250.

Green, P. N. 2005. *Methylobacterium*. In Brenner, D. J., N. R. Krieg, and J. T. Staley (eds.). "Bergey's Manual of Systematic Bacteriology. Volume two, The Proteobacteria. Part C, The alpha-, beta-, delta-, and epsilonproteobacteria." Second edition. Springer, New York. Pages 567-571.

Green, P. N. 2006. *Methylobacterium*. In Dworkin, M., S. Falkow, E. Rosenberg, K.-H. Schleifer, and E. Stackebrandt (eds.). "The Prokaryotes. A Handbook on the Biology of Bacteria. Volume 5. Proteobacteria: Alpha and Beta Subclasses." Third edition. Springer, New York. Pages 257-265.

Holland, M. A. 1997. *Methylobacterium* and plants. Recent. Res. Devel. in Plant Physiol. 1: 207-213.

Holland, M. A., and J. C. Polacco. 1994. PPFMs and other covert contaminants: Is there more to plant physiology than just plant? Annu. Rev. Plant Physiol. Plant Mol. Biol. 45: 197-209.

Kutschera, U. 2007. Plant-associated methylobacteria as co-evolved phytosymbionts. A hypothesis. Plant Signal Behav. 2: 74-78.

Lidstrom, M. E. 2006. Aerobic methylotrophic prokaryotes. In Dworkin, M., S. Falkow, E. Rosenberg, K.-H. Schleifer, and E. Stackebrandt (eds.). "The Prokaryotes. A Handbook on the Biology of Bacteria. Volume 2. Ecophysiology and biochemistry." Third edition. Springer, New York. Pages 618-634.

Madhaiyan, M., S. Poonguzhali, H. S. Lee, K. Hari, S. P. Sundaram, and T. M. Sa. 2005. Pink-pigmented facultative methylotrophic bacteria accelerate germination, growth and yield of sugarcane clone Co86032 (*Saccharum officinarum* L.) Biol. Fertil. Soils 41: 350-358.

Madhaiyan, M., S. Poonguzhali, M. Senthilkumar, S. Seshadri, H. Chung, J. Yang, S. Sundaram, and T. Sa. 2004. Growth promotion and induction of systemic resistance in rice cultivar C0-47 (*Oryza sativa* L.) by *Methylobacterium* spp. Bot. Bull. Acad. Sin. 45: 315-324.

Madhaiyan, M., S. Poonguzhali, and T. Sa. 2007. Influence of plant species and environmental conditions on epiphytic and endophytic pink-pigmented facultative methylotrophic bacterial populations associated with field-grown rice cultivars. J Microbiol Biotechnol. 2007 October; 17(10):1645-54.

Stanier, R. Y., N. J. Palleroni, and M. Doudoroff. 1966. The aerobic pseudomonads: A taxonomic study. J. Gen. Microbiol. 43: 159-271.

Sy, A., Giraud, E., Jourand, P., Garcia, N., Willems, A., De Lajudie, P., Prin, Y., Neyra, M., Gillis, M., Boivin-Masson, C., and Dreyfus, B. 2001. Methylotrophic *Methylobacterium* Bacteria Nodulate and Fix Nitrogen in Symbiosis with Legumes. Jour. Bacteriol. 183(1):214-220, Sy, A., A. C. J. Timmers, C. Knief, and J. A. Vorholt. 2005. Methylotrophic metabolism is advantageous for *Methylobacterium extorquens* during colonization of *Medicago truncatula* under competitive conditions. Appl. Environ. Microbiol. 71: 7245-7252.

Vogel, H. J., and D. M. Bonner. 1956. Acetylornithinase of *Escherichia coli*: Partial purification and some properties. J. Biol. Chem. 218: 97-106.

Whittenbury, R., Si. Davies, and J. F. Wilkinson. 1970. Enrichment, isolation and some properties of methane-utilizing bacteria. J. Gen. Microbiol. 61: 205-218.

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for obtaining a *Methylobacterium* preparation comprising: (i) combining *Methylobacterium*, an aqueous liquid, and a plant oil to obtain an inoculated culture media comprising a mono-culture or co-culture of *Methylobacterium* in an emulsion comprising a continuous phase comprising the aqueous liquid, and a dispersed phase comprising the plant oil at 0.02% to 20% of said emulsion by mass; and (ii) incubating the inoculated media under conditions sufficient to provide for growth of the *Methylobacterium*, wherein the dispersed phase provides for an increased yield of said *Methylobacterium* relative to a yield obtained by growing the *Methylobacterium* under identical conditions except for being grown in a non-emulsion medium that comprises a liquid corresponding to that of the continuous phase; and (iii) harvesting *Methylobacterium* grown in the emulsion, thereby obtaining a *Methylobacterium* preparation.

2. The method of claim 1, wherein the plant oil is selected from the group consisting of corn oil, soybean oil, cotton oil, peanut oil, sunflower oil, olive oil, flax oil, coconut oil, palm oil, rapeseed oil, sesame seed oil, safflower oil, and combinations thereof.

3. The method of claim 2, wherein the *Methylobacterium* are harvested at a titer of at least $5\times10^8$ colony-forming units per milliliter.

4. The method of claim 2, wherein the emulsion further comprises an agriculturally acceptable adjuvant or agriculturally acceptable excipient.

5. The method of claim 1, wherein the emulsion further comprises an emulsifier in an amount sufficient to stabilize the emulsion.

6. The method of claim 5, wherein the emulsifier is selected from the group consisting of thickeners, surfactants, and combinations thereof.

7. The method of claim 1, wherein the combining comprises inoculating an emulsion comprising the aqueous liquid and plant oil with *Methylobacterium.*

8. The method of claim 1, wherein the combining comprises inoculating the aqueous liquid with *Methylobacterium*, introducing the plant oil, and mixing to form an emulsion.

9. The method of claim 1, wherein said emulsion does not contain a photosynthetic microorganism or wherein the emulsion further comprises one or more non-photosynthetic microorganisms of pre-determined identity other than *Methylobacterium.*

10. The method of claim 1, wherein the plant oil comprises 0.5% to 3% of said emulsion by mass.

11. The method of claim 1, wherein said plant oil comprises 1% to 3% of the emulsion by mass.

12. The method of claim 1, wherein said *Methylobacterium* is selected from the group consisting of *M. aminovorans, M. chloromethanicum, M. dichloromethanicum, M. extorquens, M. fujisawaense, M. mesophilicum, M. organophilum, M. radiotolerans, M. rhodesianum, M. rhodinum, M. thiocyanatum, M. nodulans, M. cerastii, M. gossipiicola, Methylobacterium* sp. strain LMG6378, *M. phyllosphaerae, M. oryzae, M. platani, M. populi*, and *M. zatmanii.*

13. The method of claim 1, wherein said emulsion is essentially free of contaminating microorganisms.

14. The method of claim 1, wherein said harvesting comprises recovering all or a portion of the *Methylobacterium* from the emulsion.

15. The method of claim 14, said method further comprising dehydrating the recovered portion of the *Methylobacterium*.

16. The method of claim 1, wherein the dispersed phase comprises at least about 0.5% to about 10% of said emulsion by mass.

17. The method of claim 16, wherein the dispersed phase comprises about 1% to about 5% of the emulsion by mass.

18. The method of claim 1, said method further comprising adding an agriculturally acceptable adjuvant comprising a polysaccharide to the harvested *Methylobacterium*, wherein the adjuvant promotes sticking to a seed or plant part.

* * * * *